United States Patent
Babyak et al.

(12)

(10) Patent No.: US 6,376,222 B1
(45) Date of Patent: Apr. 23, 2002

(54) RIBOFLAVIN PRODUCTION

(75) Inventors: Lyubov Ya. Babyak, Lviv (UA); Adelbert Bacher, Garching (DE); Yuriy R. Boretskyy; Vasyl V. Demchyshyn, both of Lviv (UA); Sabine Eberhardt, Ismaning (DE); Dariya Fedorovych, Lviv (UA); Holger Lüttgen, Garching; Gerald Richter, Gaimersheim, both of (DE); Adolphus van Loon, Rheinfelden (CH)

(73) Assignee: Roche Vitamins, Inc., Parsipanny, NJ (US)

( * ) Notice: Subject to any disclaimer, the term of this patent is extended or adjusted under 35 U.S.C. 154(b) by 0 days.

(21) Appl. No.: 09/299,041

(22) Filed: Apr. 23, 1999

(30) Foreign Application Priority Data

Apr. 23, 1998 (EP) .............................. 98107380

(51) Int. Cl.⁷ ................................ C12P 17/18
(52) U.S. Cl. .................... 435/119; 435/195; 435/254.2; 435/254.22; 536/23.1; 536/23.2
(58) Field of Search ........................... 435/254.11, 483; 536/23.2

(56) References Cited

U.S. PATENT DOCUMENTS 5,821,090 A    10/1998    Revuelta Doval et al. .... 435/88

FOREIGN PATENT DOCUMENTS

WO    WO 95/26406    10/1995

OTHER PUBLICATIONS

Liauta–Teglivets et al. Molecular Cloning of the GTP–Cyclohydrolase Structural Gene RIB1 of *Pichia guilliermondii* Involved in Riboflavin Biosynthesis. Yeast (1995) 11:945–952, 1995.*

Garcia–Ramirez et al. The *Saccharomyces cerevisiae* RIB4 Gene Codes for 6,7–Dimethyl–8–ribityllumazine Synthase Involved in Riboflavin Biosynthesis. Journal of Biological Chemistry (1995) 270(40): 23801–23807, 1995.*

* cited by examiner

*Primary Examiner*—Ponnathapuachuta Murthy
*Assistant Examiner*—Kathleen Kerr
(74) *Attorney, Agent, or Firm*—Bryan Cave LLP

(57) ABSTRACT

The present invention provides a transformed yeast strain containing a DNA sequence transcriptionally linked to a promoter functional in such yeast cells, which when expressed in a suitable host cell, encodes at least one polypeptide having riboflavin biosynthetic activity. Using such transformants, improved levels of riboflavin production are achieved. Processes of producing riboflavin from such transformants are also provided.

31 Claims, 16 Drawing Sheets

```
          10        20        30        40        50        60
           |         |         |         |         |         |
GTCGACTTTCACTCCGAAGGTAGGTGCGGCTGGAAGACGTCGTCCCAAGTCGTATGCGTT 70        80        90       100       110       120
           |         |         |         |         |         |
AGCTGAGAGCGACGGAAACGAAAGTGATGAAGATTACATGCTGGAATAATCCATAGCTAG 130       140       150       160       170       180
           |         |         |         |         |         |
TGTACTTGCTAATACAACCGGTAAAGCTAGCCAATTGCAGCGTTATTCACCACCGCCGTG 190       200       210       220       230       240
           |         |         |         |         |         |
GATCGGGTTAGTCACGTGAACTGGCCGTTGGGTCCTGCACGTCGCTTCATTATTCATATA 250       260       270       280       290       300
           |         |         |         |         |         |
TTAGTGAGAGTCTTCCTATATCAGTCAGCAGACGTATCGGTTGATTTCAGGTCAAAAAGA 310       320       330       340       350       360
           |         |         |         |         |         |
GAAAAGGTGGTCTTACAAAAGCGAAATAGCTGATACATTTTTACTCACAGCAGCATCATA 370       380       390       400       410       420
           |         |         |         |         |         |
TTTGTGGAACCTTTAAACTTGACTTTTCATTTCAAGCAAGTTATTTTGAAATTCAAATCA 430       440       450       460       470       480
           |         |         |         |         |         |
TTTGGAAATCAAAAAAGAACATCTAAGTTCTGAAAAATTGTACGAACAACGCTATGGCAT
                                                         METAlaSer
```

FIG. 2A

```
         490       500       510       520       530       540
          |         |         |         |         |         |
CGAAGGACATAGTACATCCGCAACCAGAGCGCCGGCACGGGTCGGAAACTCACGAATTTA
LysAspIleValHisProGlnProGluArgArgHisGlySerGluThrHisGluPheThr 550       560       570       580       590       600
          |         |         |         |         |         |
CCATGCCTCTCTTATCTCCTACATTGACACCATCCCATATTCCATCGCAAACGCCTCAAA
METProLeuLeuSerProThrLeuThrProSerHisIleProSerGlnThrProGlnIle 610       620       630       640       650       660
          |         |         |         |         |         |
TTCCTCCGGAAGTGCCAGCAGAAGTCAGGGATCGCTTGCCCCTTCCTGAAACGTTGCCTG
ProProGluValProAlaGluValArgAspArgLeuProLeuProGluThrLeuProVal 670       680       690       700       710       720
          |         |         |         |         |         |
TGGTGAAATGCATGGCGAGAGCTCGTATACCGACCACTCAGGGGCCGGAGATATTTCTCC
ValLysCysMETAlaArgAlaArgIleProThrThrGlnGlyProGluIlePheLeuHis 730       740       750       760       770       780
          |         |         |         |         |         |
ATTTGTACGAGAATAACGTTGACAATAAAGAGCATTTGGCTATTGTTTTTGGGGAAGATG
LeuTyrGluAsnAsnValAspAsnLysGluHisLeuAlaIleValPheGlyGluAspVal 790       800       810       820       830       840
          |         |         |         |         |         |
TGCGGTCGAAAACGCTCTATCAGAAACGTCCCAATGAGACCCAGCAAGATAGAATGACTC
ArgSerLysThrLeuTyrGlnLysArgProAsnGluThrGlnGlnAspArgMETThrArg 850       860       870       880       890       900
          |         |         |         |         |         |
GTGGTGCTTATGTGGGCAGATTGTTTCCTGGAAGAACCGAGGCAGACTATGACAGTGAGT
GlyAlaTyrValGlyArgLeuPheProGlyArgThrGluAlaAspTyrAspSerGluSer
```

FIG. 2B

```
      910       920       930       940       950       960
       |         |         |         |         |         |
CTAATTTGAGATTGAATTTCGATGAAAATGGCCAACTTATCAGAGATCCGAGTACCACCT
AsnLeuArgLeuAsnPheAspGluAsnGlyGlnLeuIleArgAspProSerThrThrCys 970       980       990      1000      1010      1020
       |         |         |         |         |         |
GTAGTGGTGAGCCCATTTTGGCCCGTATTCATTCGGAATGTTATACGGGGGAAACCGCAT
SerGlyGluProIleLeuAlaArgIleHisSerGluCysTyrThrGlyGluThrAlaTrp 1030      1040      1050      1060      1070      1080
       |         |         |         |         |         |
GGAGTGCTCGTTGCGATTGTGGAGAACAATTCGATGAAGCTGGTCGGTTAATGGGTGAAG
SerAlaArgCysAspCysGlyGluGlnPheAspGluAlaGlyArgLeuMETGlyGluAla 1090      1100      1110      1120      1130      1140
       |         |         |         |         |         |
CTGGGCACGGGTGTATCGTGTACCTTCGTCAGGAAGGTCGTGGAATTGGACTTGGGGAAA
GlyHisGlyCysIleValTyrLeuArgGlnGluGlyArgGlyIleGlyLeuGlyGluLys 1150      1160      1170      1180      1190      1200
       |         |         |         |         |         |
AGTTGAAGGCTTATAATTTGCAAGACTTGGGAGCGGATACCGTCCAGGCCAATTTGATGT
LeuLysAlaTyrAsnLeuGlnAspLeuGlyAlaAspThrValGlnAlaAsnLeuMETLeu 1210      1220      1230      1240      1250      1260
       |         |         |         |         |         |
TACGACATCCTGCTGATGCGAGATCTTTTTCGCTCGCTACAGCCATACTCTTGGACTTGG
ArgHisProAlaAspAlaArgSerPheSerLeuAlaThrAlaIleLeuLeuAspLeuGly 1270      1280      1290      1300      1310      1320
       |         |         |         |         |         |
GGCTCAACGAGATCAAGTTGTTGACCAACAATCCCGATAAAATTGCTGCAGTTGAGGGAA
LeuAsnGluIleLysLeuLeuThrAsnAsnProAspLysIleAlaAlaValGluGlyArg 1330      1340      1350      1360      1370      1380
       |         |         |         |         |         |
GAAACAGAGAGGTCAAGGTAGTGGAACGGGTGCCTATGGTGCCGTTGGCATGGAGAAGTG
AsnArgGluValLysValValGluArgValProMETValProLeuAlaTrpArgSerGlu
```

FIG. 2C

```
          1390      1400      1410      1420      1430      1440
            |         |         |         |         |         |
AGAATGGAATCAAGTCAAAAGAGATAGAGGGCTACTTGAGTGCTAAGATTGAAAGGATGG
AsnGlyIleLysSerLysGluIleGluGlyTyrLeuSerAlaLysIleGluArgMETGly 1450      1460      1470      1480      1490      1500
            |         |         |         |         |         |
GGCACTTGCTTGAAAAGCCACTCAAGATATGATAGAAGAGATGAAGTTAAGGACTTAAGA
HisLeuLeuGluLysProLeuLysIle *

1510      1520      1530      1540      1550      1560
            |         |         |         |         |         |
AATAAATGATGAATTAAATGACGCAAATGTCACTACTCGATTAGAGAAATAGCTATAATG 1570      1580      1590      1600      1610      1620
            |         |         |         |         |         |
AAGAATTTTGCATTTCGCAAAATTTAAGATAAATGCAAAAATTGCAAATTACGAAATATG 1630      1640      1650      1660      1670      1680
            |         |         |         |         |         |
CATATGATACAAGACAAGAAAAGACTACTAAAAGTCTCTCGAGAAGAATACTGGGTAACC 1690      1700      1710      1720      1730      1740
            |         |         |         |         |         |
TTCATCTCTTGATTATGCACTGGGGCTATTCATATGCAGATTCGCACGCCGAGGTGCAGC 1750      1760      1770      1780      1790      1800
            |         |         |         |         |         |
GTTTAGGCGCGGCTCAACGGAAGCCAACGGCCGCCACAAATTGTCCGGAAAGTCGCCGAA 1810      1820      1830      1840      1850      1860
            |         |         |         |         |         |
ACTGATCCACTGGTACCACAGCCCCATAAGAACCCCCTTTAATATTAAAAACCGTTCTTC 1870      1880      1890      1900      1910      1920
            |         |         |         |         |         |
AGCCACTTTTGATCACATTGTTTGCAGCCGCCCGTTGCTGCCATCCAAACACCACGCGTC 1930      1940      1950      1960      1970      1980
            |         |         |         |         |         |
CCCCGCACCTTTTACGGTGCCCACTGCATTGGAATTTGCATAAAACAGCCTCACGAAGTG
```

FIG. 2D

```
          1990      2000      2010      2020      2030      2040
            |         |         |         |         |         |
GATTAATTTTTAGAGCACTCAAGTCATCATGCTGCAATCTCTGCATCATGAAATGACTCC 2050      2060      2070      2080      2090      2100
            |         |         |         |         |         |
CGTTGATACAGGGAACTCAGACCGCAAGCGGCGAAGAGTCACAAGAGCGTGTGATGTGTG 2110      2120      2130      2140      2150      2160
            |         |         |         |         |         |
TCGACTCTAGAGATCCCCGGGTACCGAGCTCGAATTCACTGGCCGTCGTTTTACAACGTC 2170      2180
            |         |
GTGACTGGGAAAACCCTGGCG
```

FIG. 2E

```
         10        20        30        40        50        60
          |         |         |         |         |         |
CAATTCGAGCTCGGTACCCGGGGATCCCCCACACACCATAGCTTCAAAATGTTTCTACTC 70        80        90       100       110       120
          |         |         |         |         |         |
CTTTTTTACTCTTCCAGATTTTCTCGGACTCCGCGCATCGCCGTACCACTTCAAAACACC 130       140       150       160       170       180
          |         |         |         |         |         |
CAAGCACAGCATACTAAATTTCCCTCTTTCTTCCTCTAGGGTGTCGTTAATTACCCGTAC 190       200       210       220       230       240
          |         |         |         |         |         |
TAAAGGTTTGGAAAAGAAAAAAGAGACCGCCTCGTTTCTTTTTCTTCGTCGAAAAAGGCA 250       260       270       280       290       300
          |         |         |         |         |         |
ATAAAAATTTTTATCACGTTTCTTTTTCTTGAAATTTTTTTTTTTGATTTTTTTCTCTTT 310       320       330       340       350       360
          |         |         |         |         |         |
CGATGACCTCCCATTGATATTTAAGTCAATAAACGGTCTTCAATTTCTCAAGTTTCAGTT 370       380       390       400       410       420
          |         |         |         |         |         |
TCATTTTTCTTGTTCTATTACAACTTTTTTTACTTCTTGCTCATTAGAAAGAAAGCATAG 430       440       450       460       470       480
          |         |         |         |         |         |
CAATCTAATCTAAGGGCGAGCTCGAATTCGAACTAGTACTGCAGCACGTGACCGGCGCCT 490       500       510       520       530       540
          |         |         |         |         |         |
AGTGTTGACAATTAATCATCGGCATAGTATATCGGCATAGTATAATACGACTCACTATAG 550       560       570       580       590       600
          |         |         |         |         |         |
GAGGAAGCTTGGCGCTATGGCATCGAAGTACATAGTACATCCGCAACCAGAGCGCCGGCA
                    METAlaSerLysTyrIleValHisProGlnProGluArgArgHis 610       620       630       640       650       660
          |         |         |         |         |         |
CGGGTCGGAAACTCACGAATTTACCATGCCTCTCTTATCTCCTACATTGACACCATCCCA
GlySerGluThrHisGluPheThrMETProLeuLeuSerProThrLeuThrProSerHis
```

FIG. 3A

```
           670        680        690        700        710        720
            |          |          |          |          |          |
TATTCCATCGCAAACGCCTCAAATTCCTCCGGAAGTGCCAGCAGAAGTCAGGGATCGCTT
IleProSerGlnThrProGlnIleProProGluValProAlaGluValArgAspArgLeu 730        740        750        760        770        780
            |          |          |          |          |          |
GCCCCTTCCTGAAACGTTGCCTGTGGTGAAATGCATGGCGAGAGCTCGTATACCGACCAC
ProLeuProGluThrLeuProValValLysCysMETAlaArgAlaArgIleProThrThr 790        800        810        820        830        840
            |          |          |          |          |          |
TCAGGGGCCGGAGATATTTCTCCATTTGTACGAGAATAACGTTGACAATAAAGAGCATTT
GlnGlyProGluIlePheLeuHisLeuTyrGluAsnAsnValAspAsnLysGluHisLeu 850        860        870        880        890        900
            |          |          |          |          |          |
GGCTATTGTTTTTGGGGAAGATGTGCGGTCGAAAACGCTCTATCAGAAACGTCCCAATGA
AlaIleValPheGlyGluAspValArgSerLysThrLeuTyrGlnLysArgProAsnGlu 910        920        930        940        950        960
            |          |          |          |          |          |
GACCCAGCAAGATAGAATGACTCGTGGTGCTTATGTGGGCAGATTGTTTCCTGGAAGAAC
ThrGlnGlnAspArgMETThrArgGlyAlaTyrValGlyArgLeuPheProGlyArgThr 970        980        990       1000       1010       1020
            |          |          |          |          |          |
CGAGGCAGACTATGACAGTGAGTCTAATTTGAGATTGAATTTCGATGAAAATGGCCAACT
GluAlaAspTyrAspSerGluSerAsnLeuArgLeuAsnPheAspGluAsnGlyGlnLeu 1030       1040       1050       1060       1070       1080
            |          |          |          |          |          |
TATCAGAGATCCGAGTACCACCTGTAGTGGTGAGCCCATTTTGGCCCGTATTCATTCGGA
IleArgAspProSerThrThrCysSerGlyGluProIleLeuAlaArgIleHisSerGlu
```

FIG. 3B

```
          1090      1100      1110      1120      1130      1140
            |         |         |         |         |         |
ATGTTATACGGGGGAAACCGCATGGAGTGCTCGTTGCGATTGTGGAGAACAATTCGATGA
CysTyrThrGlyGluThrAlaTrpSerAlaArgCysAspCysGlyGluGlnPheAspGlu 1150      1160      1170      1180      1190      1200
            |         |         |         |         |         |
AGCTGGTCGGTTAATGGGTGAAGCTGGGCACGGGTGTATCGTGTACCTTCGTCAGGAAGG
AlaGlyArgLeuMETGlyGluAlaGlyHisGlyCysIleValTyrLeuArgGlnGluGly 1210      1220      1230      1240      1250      1260
            |         |         |         |         |         |
TCGTGGAATTGGACTTGGGGAAAAGTTGAAGGCTTATAATTTGCAAGACTTGGGAGCGGA
ArgGlyIleGlyLeuGlyGluLysLeuLysAlaTyrAsnLeuGlnAspLeuGlyAlaAsp 1270      1280      1290      1300      1310      1320
            |         |         |         |         |         |
TACCGTCCAGGCCAATTTGATGTTACGACATCCTGCTGATGCGAGATCTTTTTCGCTCGC
ThrValGlnAlaAsnLeuMETLeuArgHisProAlaAspAlaArgSerPheSerLeuAla 1330      1340      1350      1360      1370      1380
            |         |         |         |         |         |
TACAGCCATACTCTTGGACTTGGGGCTCAACGAGATCAAGTTGTTGACCAACAATCCCGA
ThrAlaIleLeuLeuAspLeuGlyLeuAsnGluIleLysLeuLeuThrAsnAsnProAsp 1390      1400      1410      1420      1430      1440
            |         |         |         |         |         |
TAAAATTGCTGCAGTTGAGGGAAGAAACAGAGAGGTCAAGGTAGTGGAACGGGTGCCTAT
LysIleAlaAlaValGluGlyArgAsnArgGluValLysValValGluArgValProMET 1450      1460      1470      1480      1490      1500
            |         |         |         |         |         |
GGTGCCGTTGGCATGGAGAAGTGAGAATGGAATCAAGTCAAAAGAGATAGAGGGCTACTT
ValProLeuAlaTrpArgSerGluAsnGlyIleLysSerLysGluIleGluGlyTyrLeu 1510      1520      1530      1540      1550      1560
            |         |         |         |         |         |
GAGTGCTAAGATTGAAAGGATGGGGCACTTGCTTGAAAAGCCACTCAAGATATGATAGAA
SerAlaLysIleGluArgMETGlyHisLeuLeuGluLysProLeuLysIle *
```

FIG. 3C

```
      1570       1580       1590       1600       1610       1620
        |          |          |          |          |          |
GAGATGAAGTTAAGGACTTAAGAAATAAATGATGAATTAAATGACGCAAATGTCACTACT
      1630       1640       1650       1660       1670       1680
        |          |          |          |          |          |
CGATTAGAGAAATAGCTATAATGAAGAATTTTGCATTTCGCAAAATTTAAGATAAATGCA
      1690       1700       1710       1720       1730       1740
        |          |          |          |          |          |
AAAATTGCAAATTACGAAATATGCATATGATACAAGACAAGAAAAGACTACTAAAAGTCT
      1750       1760       1770       1780       1790       1800
        |          |          |          |          |          |
CTCGAGAAGAATACTGGGTAACCTTCATCTCTTGATTATGCACTGGGGCTATTCATATGC
      1810       1820       1830       1840       1850       1860
        |          |          |          |          |          |
AGATTCGCACGCCGAGGTGCAGCGTTTAGGCGCGGCTCAACGGAAGCCAACGGCCGCCAC
      1870       1880       1890       1900       1910       1920
        |          |          |          |          |          |
AAATTGTCCGGAAAGTCGCCGAAACTGATCCACTGGTACCACAGCCCCATAAGAACCCCC
      1930       1940       1950       1960       1970       1980
        |          |          |          |          |          |
TTTAATATTAAAAACCGTTCTTCAGCCACTTTTGATCACATTGTTTGCAGCCGCCCGTTG
      1990       2000       2010       2020       2030       2040
        |          |          |          |          |          |
CTGCCATCCAAACACCACGCGTCCCCCGCACCTTTTACGGTGCCCACTGCATTGGAATTT
      2050       2060       2070       2080       2090       2100
        |          |          |          |          |          |
GCATAAAACAGCCTCACGAAGTGGATTAATTTTTAGAGCACTCAAGTCATCATGCTGCAA
      2110       2120       2130       2140       2150       2160
        |          |          |          |          |          |
TCTCTGCATCATGAAATGACTCCCGTTGATACAGGGAACTCAGACCGCAAGCGGCGAAGA
      2170       2180       2190       2200       2210       2220
        |          |          |          |          |          |
GTCACAAGAGCGTGTGATGTGTGTCGACTCTAGAGATCCCCGGGTACCGAGCTCGAATTC
      2230       2240       2250       2260
        |          |          |          |
ACTGGCCGTCGTTTTACAACGTCGTGACTGGGAAAACCCTGGCG
```

FIG. 3D

```
       10        20        30        40        50        60
        |         |         |         |         |         |
CAATTCGAGCTCGGTACCCGGGGATCCCCCACACACCATAGCTTCAAAATGTTTCTACTC 70        80        90       100       110       120
        |         |         |         |         |         |
CTTTTTTACTCTTCCAGATTTTCTCGGACTCCGCGCATCGCCGTACCACTTCAAAACACC 130       140       150       160       170       180
        |         |         |         |         |         |
CAAGCACAGCATACTAAATTTCCCTCTTTCTTCCTCTAGGGTGTCGTTAATTACCCGTAC 190       200       210       220       230       240
        |         |         |         |         |         |
TAAAGGTTTGGAAAAGAAAAAGAGACCGCCTCGTTTCTTTTTCTTCGTCGAAAAAGGCA 250       260       270       280       290       300
        |         |         |         |         |         |
ATAAAAATTTTTATCACGTTTCTTTTTCTTGAAATTTTTTTTTTTGATTTTTTTCTCTTT 310       320       330       340       350       360
        |         |         |         |         |         |
CGATGACCTCCCATTGATATTTAAGTCAATAAACGGTCTTCAATTTCTCAAGTTTCAGTT 370       380       390       400       410       420
        |         |         |         |         |         |
TCATTTTTCTTGTTCTATTACAACTTTTTTTACTTCTTGCTCATTAGAAAGAAAGCATAG 430       440       450       460       470       480
        |         |         |         |         |         |
CAATCTAATCTAAGGGCGAGCTCGAATTCGAACTAGTACTGCAGCACGTGACCGGCGCCT 490       500       510       520       530       540
        |         |         |         |         |         |
AGTGTTGACAATTAATCATCGGCATAGTATATCGGCATAGTATAATACGACTCACTATAG 550       560       570       580       590       600
        |         |         |         |         |         |
GAGGAAGCTTGGCGCTATGGCATCGAAGTACATAGTACATCCGCAACCAGAGCGCCGGCA
                 M  A  S  K  Y  I  V  H  P  Q  P  E  R  R  H 610       620       630       640       650       660
        |         |         |         |         |         |
CGGGTCGGAAACTCACGAATTTACCATGCCTCTCTTATCTCCTACATTGACACCATCCCA
 G  S  E  T  H  E  F  T  M  P  L  L  S  P  T  L  T  P  S  H
```

FIG. 4A

```
       670       680       690       700       710       720
        |         |         |         |         |         |
TATTCCATCGCAAACGCCTCAAATTCCTCCGGAAGTGCCAGCAGAAGTCAGGGATCGCTT
  I  P  S  Q  T  P  Q  I  P  P  E  V  P  A  E  V  R  D  R  L 730       740       750       760       770       780
        |         |         |         |         |         |
GCCCCTTCCTGAAACGTTGCCTGTGGTGAAATGCATGGCGAGAGCTCGTATACCGACCAC
  P  L  P  E  T  L  P  V  V  K  C  M  A  R  A  R  I  P  T  T 790       800       810       820       830       840
        |         |         |         |         |         |
TCAGGGGCCGGAGATATTTCTCCATTTGTACGAGAATAACGTTGACAATAAAGAGCATTT
  Q  G  P  E  I  F  L  H  L  Y  E  N  N  V  D  N  K  E  H  L 850       860       870       880       890       900
        |         |         |         |         |         |
GGCTATTGTTTTTGGGGAAGATGTGCGGTCGAAAACGCTCTATCAGAAACGTCCCAATGA
  A  I  V  F  G  E  D  V  R  S  K  T  L  Y  Q  K  R  P  N  E 910       920       930       940       950       960
        |         |         |         |         |         |
GACCCAGCAAGATAGAATGACTCGTGGTGCTTATGTGGGCAGATTGTTTCCTGGAAGAAC
  T  Q  Q  D  R  M  T  R  G  A  Y  V  G  R  L  F  P  G  R  T 970       980       990      1000      1010      1020
        |         |         |         |         |         |
CGAGGCAGACTATGACAGTGAGTCTAATTTGAGATTGAATTTCGATGAAAATGGCCAACT
  E  A  D  Y  D  S  E  S  N  L  R  L  N  F  D  E  N  G  Q  L 1030      1040      1050      1060      1070      1080
        |         |         |         |         |         |
TATCAGAGATCCGAGTACCACCTGTAGTGGTGAGCCCATTTTGGCCCGTATTCATTCGGA
  I  R  D  P  S  T  T  C  S  G  E  P  I  L  A  R  I  H  S  E 1090      1100      1110      1120      1130      1140
        |         |         |         |         |         |
ATGTTATACGGGGGAAACCGCATGGAGTGCTCGTTGCGATTGTGGAGAACAATTCGATGA
  C  Y  T  G  E  T  A  W  S  A  R  C  D  C  G  E  Q  F  D  E 1150      1160      1170      1180      1190      1200
        |         |         |         |         |         |
AGCTGGTCGGTTAATGGGTGAAGCTGGGCACGGGTGTATCGTGTACCTTCGTCAGGAAGG
  A  G  R  L  M  G  E  A  G  H  G  C  I  V  Y  L  R  Q  E  G
```

FIG. 4B

```
     1210      1220      1230      1240      1250      1260
       |         |         |         |         |         |
TCGTGGAATTGGACTTGGGGAAAAGTTGAAGGCTTATAATTTGCAAGACTTGGGAGCGGA
  R  G  I  G  L  G  E  K  L  K  A  Y  N  L  Q  D  L  G  A  D 1270      1280      1290      1300      1310      1320
       |         |         |         |         |         |
TACCGTCCAGGCCAATTTGATGTTACGACATCCTGCTGATGCGAGATCTTTTTCGCTCGC
  T  V  Q  A  N  L  M  L  R  H  P  A  D  A  R  S  F  S  L  A 1330      1340      1350      1360      1370      1380
       |         |         |         |         |         |
TACAGCCATACTCTTGGACTTGGGGCTCAACGAGATCAAGTTGTTGACCAACAATCCCGA
  T  A  I  L  L  D  L  G  L  N  E  I  K  L  L  T  N  N  P  D 1390      1400      1410      1420      1430      1440
       |         |         |         |         |         |
TAAAATTGCTGCAGTTGAGGGAAGAAACAGAGAGGTCAAGGTAGTGGAACGGGTGCCTAT
  K  I  A  A  V  E  G  R  N  R  E  V  K  V  V  E  R  V  P  M 1450      1460      1470      1480      1490      1500
       |         |         |         |         |         |
GGTGCCGTTGGCATGGAGAAGTAAGAATGGAATCAAGTCAAAAGAGATAGAGGGCTACTT
  V  P  L  A  W  R  S  K  N  G  I  K  S  K  E  I  E  G  Y  L 1510      1520      1530      1540      1550      1560
       |         |         |         |         |         |
GAGTGCTAAGATTGAAAGGATGGGGCACTTGCTTGAAAAGCCACTCAAGATATGATAGAA
  S  A  K  I  E  R  M  G  H  L  L  E  K  P  L  K  I  *

1570      1580      1590      1600      1610      1620
       |         |         |         |         |         |
GAGATGAAGTTAAGGACTTAAGAAATAAATGATGAATTAAATGACGCAAATGTCACTACT 1630      1640      1650      1660      1670      1680
       |         |         |         |         |         |
CGATTAGAGAAATAGCTATAATGAAGAATTTTGCATTTCGCAAAATTTAAGATAAATGCA 1690      1700      1710      1720      1730      1740
       |         |         |         |         |         |
AAAATTGCAAATTACGAAATATGCATATGATACAAGACAAGAAAAGACTACTAAAAGTCT

```
         10        20        30        40        50        60
          |         |         |         |         |         |
GGGCATGCAATTCGAGCTCGGTACCCGGGGATCCCCCACACACCATAGCTTCAAAATGTT 70        80        90       100       110       120
          |         |         |         |         |         |
TCTACTCCTTTTTTACTCTTCCAGATTTTCTCGGACTCCGCGCATCGCCGTACCACTTCA 130       140       150       160       170       180
          |         |         |         |         |         |
AAACACCCAAGCACAGCATACTAAATTTCCCTCTTTCTTCCTCTAGGGTGTCGTTAATTA 190       200       210       220       230       240
          |         |         |         |         |         |
CCCGTACTAAAGGTTTGGAAAAGAAAAAGAGACCGCCTCGTTTCTTTTTCTTCGTCGAA 250       260       270       280       290       300
          |         |         |         |         |         |
AAAGGCAATAAAAATTTTTATCACGTTTCTTTTTCTTGAAATTTTTTTTTTGATTTTTT 310       320       330       340       350       360
          |         |         |         |         |         |
TCTCTTTCGATGACCTCCCATTGATATTTAAGTCAATAAACGGTCTTCAATTTCTCAAGT 370       380       390       400       410       420
          |         |         |         |         |         |
TTCAGTTTCATTTTTCTTGTTCTATTACAACTTTTTTTACTTCTTGCTCATTAGAAAGAA 430       440       450       460       470       480
          |         |         |         |         |         |
AGCATAGCAATCTAATCTAAGGGCGAGCTCGAATTCGAACTAGTACTGCAGCACGTGACC 490       500       510       520       530       540
          |         |         |         |         |         |
GGCGCCTAGTGTTGACAATTAATCATCGGCATAGTATATCGGCATAGTATAATACGACTC 550       560       570       580       590       600
          |         |         |         |         |         |
ACTATAGGAGGAAGCTTGGCGCTATGGCATCGAAGTACATAGTACATCCGCAACCAGAGC
                        M   A   S   K   Y   I   V   H   P   Q   P   E 610       620       630       640       650       660
          |         |         |         |         |         |
GCCGGCACGGGTCGGAAACTCACGAATTTACCATGCCTCTCTTATCTCCTACATTGACAC
 R   R   H   G   S   E   T   H   E   F   T   M   P   L   L   S   P   T   L   T
```

FIG. 5A

```
         670         680         690        700         710         720
          |           |           |          |           |           |
CATCCCATATTCCATCGCAAACGCCTCAAATTCCTCCGGAAGTGCCAGCAGAAGTCAGGG
 P  S  H  I  P  S  Q  T  P  Q  I  P  P  E  V  P  A  E  V  R 730         740         750        760         770         780
          |           |           |          |           |           |
ATCGCTTGCCCCTTCCTGAAACGTTGCCTGTGGTGAAATGCATGGCGAGAGCTCGTATAC
 D  R  L  P  L  P  E  T  L  P  V  V  K  C  M  A  R  A  R  I 790         800         810        820         830         840
          |           |           |          |           |           |
CGACCACTCAGGGGCCGGAGATATTTCTCCATTTGTACGAGAATAACGTTGACAATAAAG
 P  T  T  Q  G  P  E  I  F  L  H  L  Y  E  N  N  V  D  N  K 850         860         870        880         890         900
          |           |           |          |           |           |
AGCATTTGGCTATTGTTTTTGGGGAAGATGTGCGGTCGAAAACGCTCTATCAGAAACGTC
 E  H  L  A  I  V  F  G  E  D  V  R  S  K  T  L  Y  Q  K  R 910         920         930        940         950         960
          |           |           |          |           |           |
CCAATGAGACCCAGCAAGATAGAATGACTCGTGGTGCTTATGTGGGCAGATTGTTTCCTG
 P  N  E  T  Q  Q  D  R  M  T  R  G  A  Y  V  G  R  L  F  P 970         980         990       1000        1010        1020
          |           |           |          |           |           |
GAAGAACCGAGGCAGACTATGACAGTGAGTCTAATTTGAGATTGAATTTCGATGAAAATG
 G  R  T  E  A  D  Y  D  S  E  S  N  L  R  L  N  F  D  E  N 1030        1040        1050       1060        1070        1080
          |           |           |          |           |           |
GCCAACTTATCAGAGATCCGAGTACCACCTGTAGTGGTGAGCCCATTTTGGCCCGTATTC
 G  Q  L  I  R  D  P  S  T  T  C  S  G  E  P  I  L  A  R  I 1090        1100        1110       1120        1130        1140
          |           |           |          |           |           |
ATTCGGAATGTTATACGGGGGAAACCGCATGGAGTGCTCGTTGCGATTGTGGAGAACAAT
 H  S  E  C  Y  T  G  E  T  A  W  S  A  R  C  D  C  G  E  Q 1150        1160        1170
          |           |           |
TCGATGAAGCTGGTCGGTTAATGGGTGAAGCTGGG
 F  D  E  A  G  R  L  M  G  E  A  G
```

FIG. 5B

RIBOFLAVIN PRODUCTION

FIELD OF THE INVENTION

The present invention provides for improved riboflavin production. In particular, the invention provides transformed yeast strains and processes for producing riboflavin.

BACKGROUND OF THE INVENTION

Derivatives of riboflavin (the flavocoenzymes FMN and FAD) are universally required for redox reactions in all cellular organisms. Riboflavin (vitamin $B_2$) is produced by all plants and by many microorganisms (Demain A. L. Riboflavin over synthesis. Ann. Rev. Microbiol. 1972, 26, 369). The compound is not produced in vertebrates. Riboflavin is therefore an essential nutrient for man and animals.

Riboflavin may be produced by chemical synthesis and by various fermentation procedures using, for example, strains of Bacillus (e.g., *Bacillus subtilis*), the ascomycetes *Ashbya gossypii* and *Eremothecium ashbyi* (Demain A. L. Riboflavin Over Synthesis. Ann. Rev. Microbiol. 1972, 26, 369 and Mitsuda H, Nakajima K., Effects of 8-azaguanine on Riboflavin Production and on the Nucleotide Pools in Non-Growing Cells of *Eremothecium ashbyii*. J. Nutr Sci Vitaminol (Tokyo) 1973; 19(3):215–227), various yeast strains such as *Candida guilliermondii, Candida famata* (F. W. Tanner, Jr., C. Vojnovich, J. M. Van Lanen. Riboflavin Production by Candida Species. Nature, 1945, 101 (2616) :180–181) and related strains, as well as other microorganisms.

The pathway of riboflavin biosynthesis in yeast is shown in FIG. 1. The recursors for the biosynthesis of riboflavin are guanosine triphosphate (GTP) and ribulose 5-phosphate. One mole of GTP and two moles of ribulose 5-phosphate are required to biosynthetically generate one mole of riboflavin.

In the yeast *Saccharomyces cerevisiae*, the biosynthesis of riboflavin requires at least six genes, specifically the genes RIB1, RIB2, RIB3, RIB4, RIB5 and RIB7 (Oltmanns O., Bacher A., Lingens F. and Zimmermann F. K., Biochemical and Genetic Classification of Riboflavin Deficient Mutants of *Saccharomyces cerevisiae*. Mol. Gen. Genet. 1969, 105, 306). In *C. guilliermondii*, the biosynthesis of riboflavin has also been reportedly shown to require the products of at least six genes, specifically the genes RIB1, RIB2, RIB3, RIB4, RIB5 and RIB6 (Shavlovskyy, G. M., Sibirnyy, A. A., Kshanovs'ka, B. V. Genetical classification of *C. guilliermondii* riboflavin auxotroph mutants. Genetika 15, 1561–1568, 1979). The enzymes specified by these *C. guilliermondii* genes and their roles in the biosynthetic pathway are also summarized in FIG. 1 and Table 1. In contrast to the situation in *B. subtilis*, the riboflavin biosynthetic genes are not clustered in the eucatyotes *S. cerevisiae* and *C. guilliermondii*.

TABLE 1

Enzymes and Genes of the Riboflavin Pathway

| | | Gene | | |
|---|---|---|---|---|
| | Enzyme | S. cerevisiae | C. guilliermondii | E. coli |
| A | GTP cyclohydrolase | RIB1 | RIB1 | ribA |
| B | bacterial deaminase | | | ribD |
| C | yeast reductase | RIB7 | RIB2 | |
| D | yeast deaminase | RIB2 | RIB3 | |
| E | bacterial reductase | | | ribD |

TABLE 1-continued

Enzymes and Genes of the Riboflavin Pathway

| | | Gene | | |
|---|---|---|---|---|
| | Enzyme | S. cerevisiae | C. guilliermondii | E. coli |
| F | unknown phosphatase | | | |
| G | lumazine synthase | RIB4 | RIB5 | ribE |
| H | riboflavin synthase | RIB5 | RIB7 | ribC |
| I | 3,4-dihydroxy-2-buta non 4-phosphate synthase | RIB3 | RIB6 | ribB |

The initial step in the riboflavin biosynthetic pathway is the opening of the imidazole ring of GTP catalyzed by the enzyme, GTP cyclohydrolase II. The product of this enzyme has been reported to be 2,5-diamino-6-ribosylamino-4(3H)-pyrimidinone 5'-phosphate. This intermediate is converted to 5-amino-6-ribitylamino-2,4(1H,3H)-pyrimidinedione by a sequence of side chain reduction, ring deamination and dephosphorylation reactions. The enzyme involved in the dephosphorylation of 5-amino-6-ribitylamino 5'-phosphate is still unknown.

The conversion of 5-amino-6-ribitylamino-2,4(1H,3H)-pyrimidinedione to 6,7-(1dimethyl-8-ribityllumazine by the enzyme, 6,7-dimethyl-8-ribityllumazine synthase, requires a second substrate, 3,4-dihydroxy-2-butanone 4-phosphate, which is obtained from ribulose 5-phosphate by the catalytic action of 3,4-dihydroxy-2-butanone-4-phosphate synthase. Finally, 6,7-dimethyl-8-ribityllumazine is converted to riboflavin by a dismutation reaction catalyzed by riboflavin synthase. The sequence of the RIB1 gene directing the synthesis of GTP cyclohydrolase II, the initial enzyme of the riboflavin pathway, reportedly has been established in the yeast, *C. guilliermondii* (Liauta-Teglivets, O., Hasslacher, M., Boretskyy, Y., Kohlwein, S. D., Shavlovskii, G. M. Molecular cloning of the GTP cyclohydrolase. Structural gene RIB1 of *Pichiia guilliermondii* involved in riboflavin biosynthesis. Yeast 11, 945–952, 1995).

Recombinant strains of *Bacillus subtilis* used in the production of riboflavin by fermentation have been reportedly described, e.g. in EP 405 370. These strains carry the riboflavin operon under the control of a strong promoter directing the production of the cognate enzymes. The gene constructs of the riboflavin operon under the control of a strong; promoter may be present at one or several different locations on the *B. subtilis* chromosome. The incorporation of an additional gene of the riboflavin pathway under the control of a strong promoter at a separate locus on the *B. subtilis* chromosome reportedly has also been shown to increase the yield of riboflavin obtained by fermentation. See, EP 821 063.

Whereas the production of riboflavin by native strains of yeasts such as *C. guilliermondii* have been reported, these reports suffer from the drawback that relatively small amounts of riboflavin are produced therefrom. Heretofore, recombinant DNA technology has not been applied to over-express riboflavin biosynthetic genes in *C. guillietmondii* or in related flavinogenic yeasts.

SUMMARY OF THE INVENTION

The invention is a recombinant DNA construct used to transform yeast strains which over-produce riboflavin.

More specifically, the present invention provides a yeast strain transformed by a recombinant DNA sequence such as a DNA sequence which, upon expression in a suitable host cell, encodes at least one polypeptide with riboflavin biosynthetic activity and which DNA sequence is transcriptionally linked to a promoter that is functional in such a yeast strain.

Another embodiment of the invention is a transformed yeast strain which belongs to the group of flavinogenic yeasts which over-produce riboflavin under conditions of iron starvation.

A further embodiment of the present invention is a transformed yeast strain wherein the polypeptide encoding DNA sequence is isolated or derived from yeast, preferably a flavinogenic yeast which over-produces riboflavin under conditions of iron starvation, such as Candida, e.g. *Candida guilliermondii* or *Candida famata*.

Another embodiment of the present invention is a yeast strain wherein the polypeptide encoding DNA sequence encodes a protein with GTP cyclohydrolase II activity and is selected from the following DNA sequences:

a) the DNA sequence as shown in FIG. 4 or its complementary strand;

b) DNA sequences which hybridize under standard conditions to the protein coding regions of the DNA sequences defined in (a) or fragments thereof; and c) DNA sequences which, but for the degeneracy of the genetic code, would hybridize to the DNA sequences defined in (a) and (b).

Another embodiment is a yeast strain transformed with a DNA construct as set forth above, wherein the promoter is the TEF *S. cerevisiae* promoter.

Another embodiment is a process for producing riboflavin by culturing a yeast strain as set forth above under suitable culture conditions to express riboflavin and then isolating the riboflavin from the medium or the yeast strain.

Another embodiment of the present invention is a process for producing riboflavin by mixing the isolated riboflavin with one or more suitable food or feed ingredients to form a food or feed composition.

Another embodiment is an isolated and purified DNA molecule which encodes a polypeptide with riboflavin biosynthetic activity isolated from a yeast strain and which encodes a polypeptide with riboflavin biosynthetic activity that is encoded by a nucleotide sequence including the DNA sequence in FIG. 4 and functionally equivalent fragments, mutants and derivatives thereof.

Another embodiment is a process for producing a yeast cell which over-expresses riboflavin. This process includes (a) identifying a nucleotide sequence coding for a polypeptide having riboflavin biosynthetic activity; (b) incorporating the nucleotide sequence into an expression cassette; (c) transforming a yeast cell culture with the expression cassette; (d) selecting a transformant which over-expresses riboflavin; (e) culturing the transformant in a culture medium; and (f) recovering riboflavin from the transformant and/or the culture medium.

BRIEF DESCRIPTION OF THE DRAWINGS

FIG. 2A–2E is the nucleotide sequence of a 2.18 kb SalI fragment of *C. guilliermondii* isolated from p19R1.

FIG. 3A–3D is the nucleotide sequence of the pTC2 insert.

FIG. 4A–4C is the nucleotide sequence of the pTCdXS-2 insert.

FIG. 5A–5B is a PCR fragment containing base pairs 1–1,168 of FIG. 4.

DETAILED DESCRIPTION OF THE INVENTION

Figure 1:
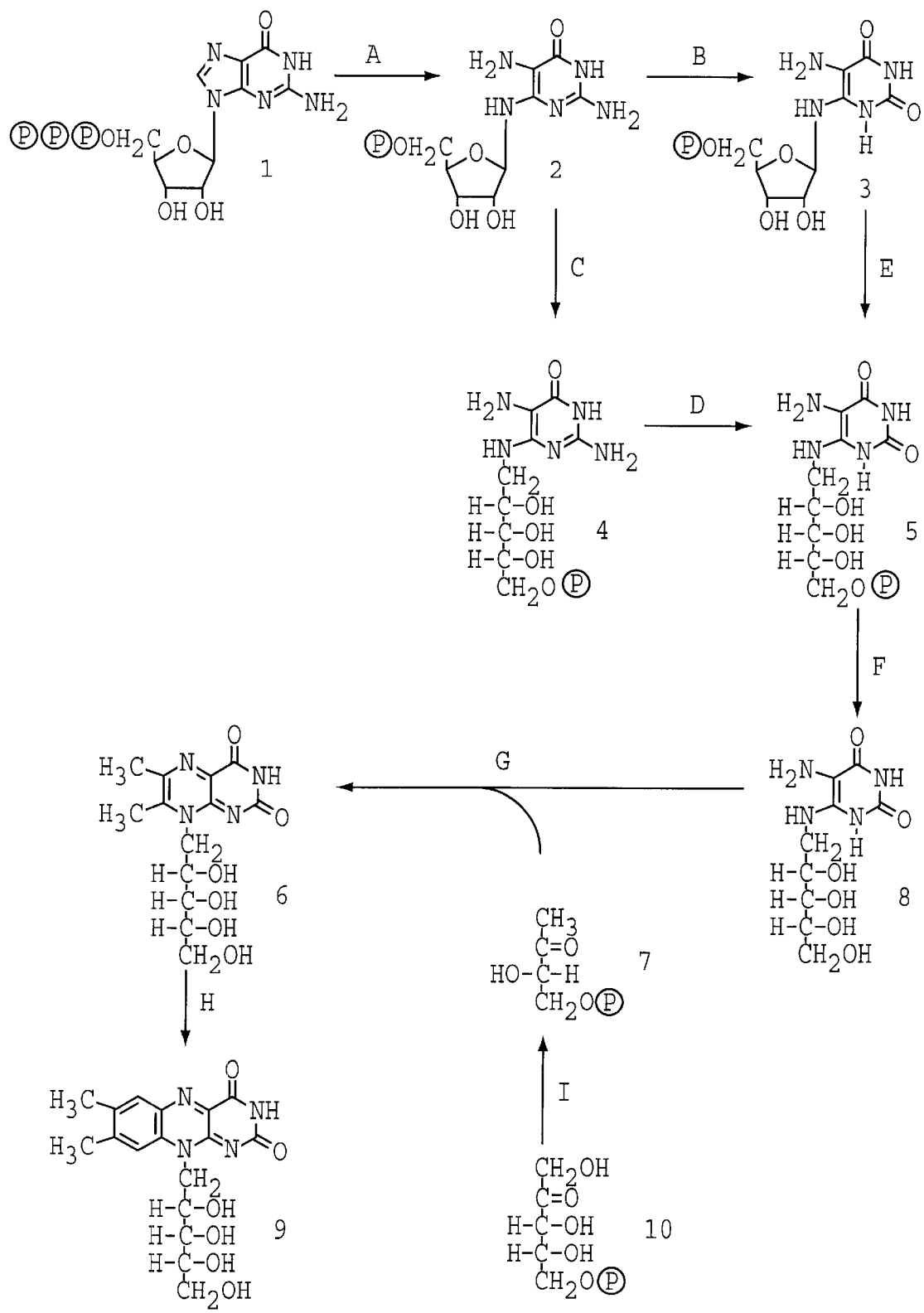
FIG. 1 is a schematic of the riboflavin biosynthesis pathway in yeast.

All *C. guilliermondii* strains used in the practice of the present invention are derivatives of the *C. guilliermondii* strain obtained from the American Type Culture Collection (ATCC) under accession No. ATCC 9058 (Sibirny, A. A., Zharova, V. P., Kshitnovskaya, B. V., Shavlovsky, G. M. Selection of a genetic line of yeast *Pichia guilliermondii* capable to formation of significant amount of spores. Tsytologia i genetika 11, 330–333, 1977). *Candida guilliermondii* (ATCC 9058) was redeposited as a Budapest Treaty deposit on Apr. 1, 1998 and was assigned accession No. ATCC 74437

*Candida guilliermondii* is representative of the yeast species which overproduce riboflavin under conditions of iron starvation. As used herein, the phrase "iron starvation" is intended to mean that the culture media contains less than about 0.01 mg of $Fe^{(2+)}$ per liter of medium, whereas the medium would normally contain about 0.2 mg/L.

The group of such yeast which overproduce riboflavin under conditions of iron starvation also includes, for example, *Schwanniomyces occidentalis*, (or called *Debaryomyces occidentalis*) *Debaryomyces kloeckeri*, *Torulopsis candida* and *Candida famata*. The latter species is preferred for industrial production of riboflavin.

In the present invention, the following are examples of flavinogenic yeast which may be used: Schwanniomyces, preferably *Schwanniomyces occidentalis*; Debaryomyces, preferably *Debaryomyces kloeckeri*; Torulopsis, preferably *Torulopsis candida*; Candida, preferably *Candida guilliermondii* or *Candida famata* (Logvinenko et al., Ukrainskii Biokhimicheskii Zhurnal 61(1), 28–32, 1989; Logvinenko et al., Mikrobiologiya 57(2), 181–186, 1988 and Nakase and Suzuki, Journal of General and Appl. Microbiology 31(1), 49–70 (1985).

The taxonomic assignments of yeast species vary depending upon who does the classification, as is known by one skilled in the art. A typical taxonomic assignment for a yeast useful in the present invention is as follows: *Candida famata—Debaryomyces hansenii—Torulaspora hansenii, Candida guilliermondii—Pichia guilliermondii—Yamadazyma guilliermondii* are used as synonyms.

These microorganisms may be used in the practice of the present invention, either as host cells or as a source for the isolation of DNA sequences. These microorganisms are available from depository authorities, e.g. the American Type Culture Collection (ATCC), the Centraalbureau voor Schimmelcultures (CBS) or the Deutsche Sammlung für Mikroorganismen und Zellkulturen GmbH (DSM) or any other depository authority as listed in the Journal "Industrial Property" (1991) 1, pages 29–40.

DNA sequences useful in the practice of the present invention and encoding a polypeptide with riboflavin biosynthetic activity may be obtained from any microorganism known to produce riboflavin. For example, the cloning of a GTP cyclohydrolase II gene using a marker rescue strategy has been previously described. See for example, Biosynthesis of riboflavin. Cloning, sequencing, mapping and expression of the gene coding for GTP cyclohydrolase II of Escherichia coli, G. Richter, H. Ritz, G. Katzenmeier, R.

Volk, A. Kohnle, F. Lottspeich, D. Allendorf and A. Bacher. J. Bacteriol. 175, 4045–4051 (1993).

As used herein, the phrase "DNA sequence" is intended to include genomic and cDNA sequences generated by methods known to one skilled in the art including the well known PCR-Technology. The principles of the polymerase chain reaction (PCR) method are outlined, for example, by White et al., Trends in Genetics, 5, 185–189 (1989), whereas improved methods are described, e.g. in Innis et al. (PCR Protocols: A guide to Methods and Applications, Academic Press, Inc. (1990). Each of these documents is hereby incorporated by reference as if recited in full herein.

The sequence information needed for the design of the PCR-primers used in the present invention may be obtained from any sequence data base, such as, for example Genbank (Intelligenetics, California, USA), European Bioinformatics Institute (Hinston Hall, Cambridge, GB), NBRF (Georgetown University, Medical Center, Washington DC, USA) and Vecbase (University of Wisconsin, Biotechnology Center, Madison, Wis., USA).

Once such a DNA sequence has been obtained, it may be expressed in any desirable host directly or using various expression cassettes, such as plasmids and the like. The riboflavin biosynthetic activity of the encoded polypeptide may be determined by any assay known to one skilled in the art and described, for example, in Bacher A., G. Richter, H. Ritz, S. Eberhardt, M. Fisher and C. Krieger, Biosynthesis of Riboflavin: GTP Cyclohydrolase II, Deaminase, and Reductase. Methods in Enzymology 1997; 280: 382–389; K. Kis, R. Volk and A. Bacher, Biosynthesis of riboflavin. Studies on the Reaction Mechanism of 6,7-dimethyl-8-ribityllumazine Synthase. Biochemistry 1995, 34, 2883;–2892; Logvinenko E. M., Shavlovskii G. M., Zakal'skii A. E., Kontorovskaia Niu. Properties of 2,5-diamino-4-oxy-6-ribosylaminopyrimidine-5'-phosphate Reductase, an Enzyme of the Second Stage of Flavinogenesis in *Pichia guilliermondii* Yeast Ukr Biokkhim Zh 1989 Jul; 61(4): 47–54; G. Richter, M. Fischer, C. Krieger, S. Eberhardt, H. Lüttgen, I. Gerstenschlaiger and A. Bacher. Biosynthesis of riboflavin. Characterization of the Bifunctional Deaminase/Reductase of *Escherichia coli* and *Bacillus subtilis*. J. Bacteriol. 1997, 179, 2022–2028; and K. Ritsert, D. Turk, R. Huber, R. Ladenstein, K. Schmidt-Bäse and A. Bacher. Studies on the Lumazine Synthase/Riboflavin Synthase Complex of *Bacillus subtilis*. Crystal Structure Analysis of Reconstituted Icosahedral β Sub Unit Capsied at 2.4 Å resolution. J. Mol. Biol. 1995, 253, 151–167, all of which are hereby incorporated by reference as if recited in full herein.

The DNA sequences used in the present invention include at least one DNA sequence which encodes a polypeptide having riboflavin biosynthetic activity. In the present invention, more than one polypeptide (e.g., one or more enzymes of the riboflavin biosynthetic pathway) may be encoded by such DNA sequences and one or more of the enzymes may be encoded by DNA sequences of different species of origin or can be of partial or total synthetic origin, as long as each DNA sequence codes for a polypeptide that possesses riboflavin biosynthetic activity (i.e., codes for an enzyme in the riboflavin biosynthetic pathway). One example of such a DNA sequence is set forth in SEQ ID NO:5. This DNA sequence codes for a GTP cyclohydrolase II. Moreover, in the present invention, DNA sequences which hybridize under standard conditions to this DNA sequence and encode such a GTP cyclohydrolase are also useful for the practice of the present invention.

As used herein, the phrase "standard conditions" when referring to DNA hybridization and hybridization washes are those conditions which are generally used by one skilled in the art to detect specific hybridization signals and which are described, e.g. by Sambrook et al., "Molecular Cloning" second edition, Cold Spring Harbor Laboratory Press 1989, New York, which is hereby incorporated by reference as if recited in full herein. Preferably, in the present invention so called "stringent" hybridization and non-stringent washing conditions are used. Such conditions are described, e.g. in Sambrook et al. supra.

For example, in the present invention, high stringency hybridization and wash conditions are those in which 0.1× SSC is used. Such conditions are useful for identifying DNA from a source containing an exact copy of the DNA of interest. As used herein, low stringency hybridization and wash conditions are those in which 0.5×SSC is used. Such conditions are useful for identifying sources of DNA which are homologous to the DNA of interest.

As used herein, the phrase "fragment of the DNA sequences" means a fragment which codes for a polypeptide still having the enzymatic activity as specified above.

The present invention also includes a DNA molecule coding for a protein or polypeptide having riboflavin biosynthetic activity, which DNA is a fragment, mutant, or degenerate form of the native gene, so long as the expressed protein or polypeptide retains the riboflavin biosynthetic activity.

For purposes of the present invention, mutant DNAs are made by a variety of methods known in the art, such as for example, site-directed mutagenesis and the like. In the present invention, such mutants, however, maintain their riboflavin biosynthetic activity.

As is also known, it is possible to substitute amino acids in a sequence with equivalent amino acids. Groups of amino acids known normally to be equivalent are:

(a) Ala(A) Ser(S) Thr(T) Pro(P) Gly(G);
(b) Asn(N) Asp(D) Glu(E) Gln(Q);
(c) His(H) Arg(R) Lys(K);
(d) Met(M) Leu(L) Ile(I) Val(V); and
(e) Phe(F) Tyr(Y) Trp(W).

Substitutions, additions and/or deletions in the DNA sequences of the present invention may be made as long as the protein of the invention continues to satisfy the criteria described above, i.e., have a riboflavin biosynthetic activity. An amino acid sequence that is substantially the same as another sequence, but that differs from the other sequence by means of one or more substitutions, additions and/or deletions is considered to be an equivalent sequence, i.e., a derivative thereof. Preferably, less than 25%, more preferably less than 10%, of the number of amino acid residues in a sequence are substituted for, added to, or deleted from the fragments in the derivative sequences of the invention.

To over-express proteins encoded by the DNA sequences of the present invention, these sequences may be transcriptionally linked to promoters which are functional in the desired yeast, such as for example, the *S. cerevisiae* TEF-promoter (see Example 2), the pho5-promoter (Vogel et al., Mol. Cell. Biol., 2050–2057 (1989); Rudolph and Hinnen, Proc, Natl. Acad. Sci. 84, 1340–1344 (1987)), the gap-promoter, the aox1-promoter (Koutz et al., Yeast 5, 167–177 (1989); Sreekrishna et al., J. Basic Microbiol. 28, 265–278 (198E;)), the FMD promoter (Hollenberg et al., EP 299108) or the MOS-promoter (Ledeboer et al., Nucleic Acids Res. 13, 3063–3082 (1985)). As used herein, "transcriptionally linked" means that the promoter or another expression control sequence (regulatory element etc.) is operatively linked to the DNA sequence or fragment to be expressed. Such promoters or expression control sequences are inserted into, e.g., a vector in order to control and to regulate the cloned DNA sequence.

For purposes of the present invention, the terms "over-express" or "over-produce" are intended mean that the DNA sequences and the polypeptides produced therefrom are synthesized in amounts greater than wild type yeast. Thus, as set forth in more detailed in the examples below, using the recombinant constructs of the present invention enzyme levels at least twice that of the wild type (*C. guilliermondii* L2) controls are achievable.

The DNA sequences useful for the practice of the present invention may also include so called "ARS" elements (autonomously replicating sequence) as described, e.g. in Example 1.

The present invention also includes a process for producing riboflavin. This process includes culturing a yeast strain as described above in a culture media conducive to its growth; (b) expressing riboflavin from the yeast strain; and (c) recovering riboflavin from the medium or the yeast strain. Examples of such processes are set forth in detail in the examples below.

This process also includes mixing the isolated riboflavin with a food or feed ingredient to produce a food or feed composition. Thus, the recovered riboflavin may be further purified or directly combined with various food stuffs or animal feed as, e.g. a nutritional supplement. Moreover, the riboflavin produced in accordance with the present invention may also be used alone or in combination with other pharmaceuticals in a variety of forms known in the art.

The following examples are set forth to illustrate the compositions and processes of the present invention. These examples are provided for purposes of illustration only and are not intended to be limiting in any sense.

EXAMPLES

In the present examples, if not specifically indicated or referred to by references, standard procedures were used as described, e.g. in Sambrook et al. "Molecular Cloning," (s.a.) and Cregg, J. M., K. J. Barriner, A. Y. Hessler, and K. R. Madden (1985). *Pichia pastoris* was used as a host system for transformation according to the procedures in Mol. Cell. Biol. 5, 3376–3385.

Example 1

Autonomous Replication of Plasmid p19R1 in *C. guilliermondii*

The plasmid pFR1 carrying the RIB1 gene of *C. guilliermondii* has reportedly been described (Zakalsky at al. Genetika 26, 614–620, 1990). In order to subclone the RIB1 gene, plasmid pFR1 was digested with the restriction nuclease SalI. The resulting fragments were cloned into the SalI site of the pUC19 vector. The ligation mixture was transformed into the *E. coli* mutant strain BSV821 carrying a mutation of the ribA gene contributing to riboflavin deficiency. Colonies growing in the absence of riboflavin were isolated and were shown to contain a plasmid designated as p19R1.

The plasmid p19R1 was sequenced and was shown to contain a 2.18 kb fragment of *C. guilliermondii* DNA in the SalI site of the pUC19 vector. The sequence of this insert is shown in FIG. 2 (SEQ ID NO:1).

The DNA sequence shown in FIG. 2 carries the RIB1 gene of *C. guilliermondii*. This plasmid transforms *C. guilliermondii* mutants defective in the RIB1 gene to riboflavin prototrophy and can replicate autonomously in this yeast species. The replication was shown to be due to the presence of an autonomously replicating sequence (ARS) spanning approximately base pairs 1,542 to 1,755 in FIG. 2 and extending into the structural gene RIB1.

Example 2

Construction of a Plasmid for Hyper-Expression of the RIB1 Gene of *C. guilliermondii*

The TEF gene of the yeast *S. cerevisiae* specifies the translation elongation factor 1-alpha. This gene is reported to be transcribed in *S. cerevisiae* with high efficiency.

A DNA fragment carrying the *S. cerevisiae* TEF promoter and the 5' part of the RIB1 gene of *C. guilliermondii* was obtained by PCR amplification. Initially, a DNA sequence located upstream from the 5' end of the *S. cerevisiae* TEF gene was amplified by PCR with primers ShBle_V and TEF1_H using chromosomal DNA of *S. cerevisiae* as a template. The amplified DNA fragment (subsequently designated as the TEF promoter) includes base pairs 15,984 to 16,344 of the sequence listed under the EMBL accession number gb/U51033/YSCP9513.

Independently, a DNA fragment including the 5'-terminal part of the *C. guilliiermondii* GTP cyclohydrolase II structural gene was obtained by PCR with primers PGgtpCY_V and PGgtpCY_nco using p19R1 plasmid as a template. The amplified DNA fragment (subsequently designated 5'GTPcII) spans base pairs 460 to 1,145 of the sequence shown in FIG. 2.

Figure 6:
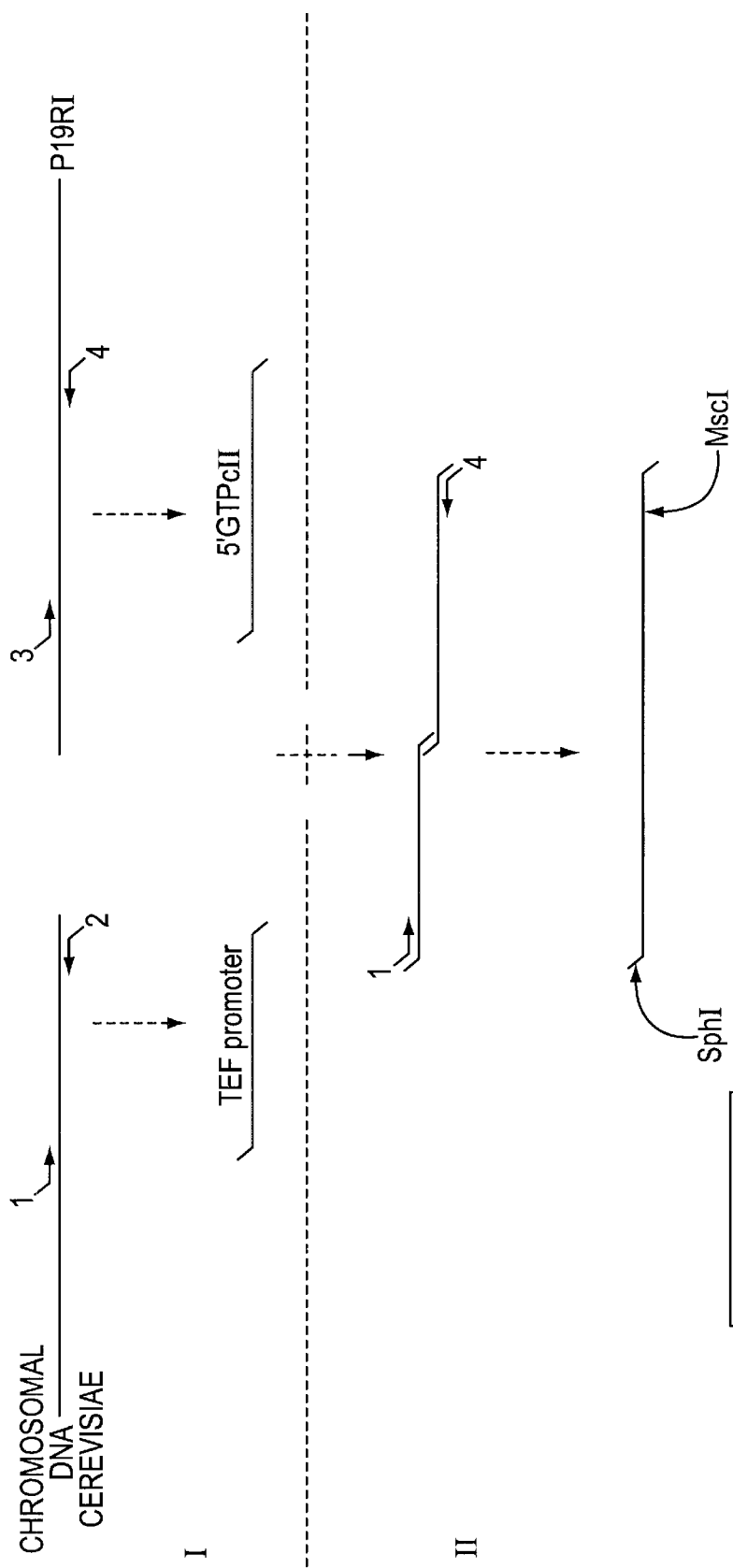
FIG. 6 is a schematic of the PCR reactions used to construct a DNA fragment containing the complete TEF promoter and the 5' part of the *C. guilliermondii* RIB1 gene.

The amplified DNA obtained in the two PCR reactions described above containing parts of the TEF gene of *S. cerevisiae* and of the 5'GTPcII were mixed, and a third PCR amplification was performed using the primers ShBle_V and PGgtpCY_nco. This reaction yielded a DNA fragment which contains the complete TEF promoter and the 5'part of the *C. guilliermondii* RIB1 gene. A schematic for this construction is set forth in FIG. 6.

All primers used in these PCRs are shown in Table 2.

TABLE 2

Nucleotide Sequences of the Primers Used

| N Primer | Sequence (5'–3') | |
|---|---|---|
| 1 ShBle_V | GGGCATGCAATTCGAGCTCGGTACCCG | (SEQ ID NO:11) |
| 2 TEF1_H | CGACTCACTATAGGAGGAAGCTTGGCGC | (SEQ ID NO:12) |
| 3 PGgtPCY_V | AGGAGGAAGCTTGGCGCTATGGCATCGAAG | (SEQ ID NO:10) |
| 4 PGgtpCY_nco | GGCTGGTCGGTTAATGGGTGAAGCTGGG | (SEQ ID NO:9) |

The sequence of the final amplified DNA is shown in FIG. 3 (SEQ ID NO: 3). The amplified DNA contains a cutting site for the restriction nuclease SphI which was introduced via the primer ShBle_V. The amplified DNA also contains a MscII site which is a feature of the RIB1 gene. The amplified DNA was digested with SphI and MscII.

The plasmid p19R1 was also digested with the same enzymes, and the PCR amplified DNA was ligated into the digested plasmid. The ligation mixture was transformed into a mutant designated Rib7 of *Escherichia coli* carrying a mutation of the ribA gene which specifies GTP cyclohydrolase II. Transformation was performed by electroporation according to the protocol of Invitrogen (Zero Background/ Kan Cloning Kit. Version A. 151204. Instruction manual. INVITROGENE).

The *E. coli* cells were plated on Luria-Broth plates supplemented with ampicillin (100 mg/ml) which did not contain riboflavin. Colonies growing on this medium were isolated and were shown to contain a plasmid designated pTC2. The sequence of the insert of the plasmid pTC2 is shown in FIG. 3.

Plasmid pTC2 was digested with XhoI and SalI restriction endonucleases yielding 4.4 kb and 0.5 kb fragments. The 4.4 kb fragment was circularized with T4 DNA ligase. The ligation mixture was transformed into the Rib7 mutant of *E. coli* carrying the RibA mutation. Transformation was achieved by electroporation. The cells were plated on Lurii-Broth plates containing ampicillin and no riboflavin as set forth above. Colonies growing on these plates were isolated and were shown to contain a plasmid pTCdXS-2. This procedure resulted in the removal of 0.5 kb base pairs from the plasmid pTC2.

The sequence of the insert of the plasmid pTCdXS-2 is shown in FIG. 4 (SEQ ID NO: 5). The open reading frame of the RIB1 gene of *C. guilliernondii* and the DNA segment representing the promoter of the TEF gene of *S. cerevisiae* are also shown in FIG. 4.

Example 3

Construction of Recombinant *C. guilliermondii* Strains

The riboflavin deficient mutant rh-21 with an apparent defect of the RIB1 gene specifying GTP cyclohydrolase II (Shavlovskyy, G. M., Sibimyy, A. A., Kshanovs'ka, B. V. Genetical classification of *C. guilliermondii* riboflavin auxotroph mutants. Genetika 15, 1561–1568, 1979) was obtained after chemical mutagenesis of the L2 strain (Id.) which was previously obtained from the ATCC 9058 *C. guilliermondii* strain.

The plasmid pTCdXS-2 was transformed into the RIB1 mutant strain rh-21 of *C. guilliermondii* by the LiCl procedure (Logvinenko, E. M., Stasiv, Yu. Z., Zlochevsky, M. L., Voronovsky, A. Ya., Beburov, M. Yu., Shavlovsky, G. M. Cloning of the RIB7 gene ncoding the riboflavin synthase of the yeast *Pichia guilliermondii*. Genetika 29, 922–927, 1993). The cells were plated on YPD medium without added riboflavin. Colonies growing without riboflavin were isolated. These colonies were monitored for GTP cyclohydrolase II activity and for riboflavin production as described below.

In particular, the prototrophic strains were monitored for the presence of DNA segments introduced with the plasmid by PCR analysis. PCR was performed using the primers ShBle_V and PGgtpCY_nco and boiled *C. guilliermondii* recombinant strain cells as template. Primer ShBle_V is complementary to the TEF promoter and primer PGgtpCY_nco is complementary to the RIB1 structural gene. Amplified DNA of the expected length (e.g., 1,175 base pairs) was obtained from all transformants isolated. The amplified DNA obtained from strain XS-3 was isolated and was sequenced by the fluorescent dideoxy terminator method. This sequence is shown in FIG. 5 (SEQ ID NO: 7) and is identical to base pairs 1 to 1,168 of the insert of plasmid pTCdXS-2.

The recombinant transformants were genetically stable. Specifically, they did not segregate riboflavin deficient subclones.

Example 4

GTP Cyclohydrolase Activity in Recombinant *C. guilliermondii* Strains

The level of GTP cyclohydrolase II activity in the recombinant strains described above was determined as follows.

The recombinant *C. guilliermondii* cells were grown aerobically in synthetic Burkholder medium supplemented with trace elements (Science 101, 180, 1945) but without asparagine for 2–3 days at 30° C. *C. guilliermondii* L2 strain (wild type) served as a control in these experiments.

Cells from the exponential growth phase were harvested by centrifugation (5000 g, 15 minutes), washed twice with 20 mM Tris HCl, pH 8.2, containing 1 mM DTT and 1 mM $MgCl_2$. The cells were stored at $-20°$ C. until use. The frozen cell mass (1–3 g) was thawed in 3–9 ml of washing buffer. The cells were disrupted by agitation with glass beads (d=0.8 mm). After centrifugation, the cell extract was dialyzed overnight against 100 volumes of washing buffer. The protein concentration was measured by the Lowry method.

The reaction mixture for each GTP cyclohydrolase assay contained 20 mM Tris HCl, pH 8.2, 3 mM DTT, 2 mM $MgCl_2$, 1 mM GTP and protein (protein concentration, 1–3 mg/ml, total volume, 4 ml). Each reaction mixture was incubated at 37° C. for 20 minutes in the dark.

After incubation, 2 ml aliquots were removed from each reaction mixture, and 2,3-butanedione was added to a final concentration of 0.5 mg/ml. The mixtures were incubated at 95° C. for 30 minutes. Blank values were processed in the same way but without added diacetyl.

Differences in specific fluorescence of both types of aliquots were determined and were used to calculate the concentrations of 6,7-dimethylpteridin and the activity of GTP cylohydrolase II. Results are shown in Table 3.

TABLE 3

Activity of GTP Cyclohydrolase II and Riboflavin Synthase in *C. guilliermondii* Recombinant Strains (Time of Growth: 40–48 h)

| N | Strain | Riboflavin synthase activity nmol mg$^{-1}$ h$^{-1}$ | GTP cyclohydrolase II activity nmol mg$^{-1}$ h$^{-1}$ | Ratio* |
|---|---|---|---|---|
| 1 | L2 (wild type) | 21.6 | 2.88 | 1.00 |
| 2 | R1-1 | n.d. | 10.08 | 3.50 |
| 3 | R1-2 | n.d. | 4.20 | 1.46 |
| 4 | R1-3 | 20.4 | 8.76 | 3.04 |
| 5 | R1-4 | 19.8 | 7.80 | 2.70 |
| 6 | R1-5 | 21.6 | 7.80 | 2.70 |
| 7 | TC-1 | 20.4 | 9.60 | 3.33 |
| 8 | TC-2 | n.d. | 8.40 | 2.92 |
| 9 | TC-3 | n.d. | 7.56 | 2.63 |
| 10 | XS-1 | 22.8 | 13.38 | 4.60 |
| 11 | XS-2 | n.d. | 12.60 | 4.37 |
| 12 | XS-3 | n.d. | 6.60 | 2.29 | n.d. not determined.
*GTP cyclohydrolase activity of recombinant strain divided by GTP cyclohydrolase activity of strain L2.

In these assays, strain L2 from which the mutant rh-21 had been derived was used control. The enzyme activity in the strain L2 was determined to be 2.9 nmol mg$^{-1}$ h$^{-1}$. No enzyme activity was found in the riboflavin deficient recipient strain rh-21 carrying a mutation of the RIB1 gene. The recombinant strains obtained by transformation with plasmid pTCdXS-2 showed enzyme levels between 6.5 and 13.4 nmol mg$^{-1}$ h$^{-1}$ Thus, the enzyme level in the recombinant strains was surprisingly 2.3–4.6-fold higher as compared with the C. guilliermondii strain L2.

The activity of riboflavin synthase was also measured in the recombinant strains. The activity of riboflavin synthase was not affected by transformation with plasmids p19R1, pTC2 or pTCdXS-2. All strains analyzed had riboflavin synthase activities in the range of 20 nmol mg$^{-1}$ h$^{-1}$ (Table 3).

Example 5

Production of Riboflavin by Recombinant C. guilliermondii Strains

C. guilliermondii strains (wild type and recombinant strains) were grown aerobically synthetic Burkholder medium supplemented with trace elements (Science 101, p. 180, (1945)) but without asparagine for 4 days at 30 ° C. (F. W. Tanner, Jr.C. Vojnovich, J. M. Van Lanen, Riboflavin Production by Candida Species. Nature, 1945, 101 (2616): 180–181)). The suspension was centrifuged. The riboflavin concentration of determined fluorometrically. Results are shown in Table 4.

TABLE 4

Riboflavin Production by Recombinant C. guilliermondii Strains (Time of Growth: 110 h, Incubation Temperature: 30° C.).

| N | Strain | Riboflavin production (mg/l) | Relative riboflavin production |
|---|---|---|---|
| 1 | L2 (wild type) | 1.2 | 1.0 |
| 4 | R1-3 | 1.4 | 1.2 |
| 5 | R1-4 | 3.6 | 3.0 |
| 6 | R1-5 | 3.0 | 2.5 |
| 7 | TC-1 | 1.4 | 1.2 |
| 9 | TC-3 | 1.3 | 1.0 |
| 12 | XS-3 | 3.6 | 3.0 |
| 13 | XS-4 | 2.0 | 1.7 |
| 14 | XS-5 | 2.3 | 1.9 |

As Table 4 indicates, the wild strain L2 produced 1.2 mg riboflavin per liter under the conditions described. The recombinant strain XS-3 surprisingly produced 3-times more riboflavin (3.6 mg/l) compared to the wild type strains.

Example 6

Isolation of riboflavin

Two Erlenmeyer flasks (2.5 l) each containing 0.5 l of synthetic Burkholder medium containing trace elements but no asparagine were inoculated with the recombinant C. guilliermondii strain XS-3. The cultures were incubated with shaking at 30° C. for 50 hours. The solution was centrifuged. The supernatant was passed through a column of Florisil (4 ml bed volume) at a velocity of 500 ml/h. The column was washed with distilled water (7 ml). Riboflavin was eluted with a mixture of acetone/IM aqueous NH$_4$OH. The effluent was evaporated to dryness. The yield of riboflavin was determined photometrically as set forth in Table 4.

Example 7

Hybridization of RIB1 Gene of C. guilliermondii

The hybridization and wash conditions given in the following protocol are appropriate for a majority of probes, allowing detection of single copy genes, such as for example the RIB1 gene, from different species without significant cross-hybridization of non-homologous sequences. The hybridization system and procedures used in this example are commercially available (ECL™ direct nucleic acid labelling and detection systems (Amersham)).

Preparation of the hybridization buffer:

At room temperature, to a required volume (0.5 ml/cm$^2$) of hybridization buffer (for example a stock hybridization solution for use with labeled DNA fragment probes and nitrocellulose filters is prepared from: 80 gm dextran sulfate in 290 ml water, 320 ml deionized formamide, 160 mL 20×SSC, 2.8 ml @ M Tris-Cl, pH 7.4, 8 ml 100×Denhardts solution, 8 ml herring sperm DNA (boiled for 10 minutes) at 10 mg/ml), solid sodium chloride (analytical grade) is added by mixing to a concentration of about 0.5M NaCl which is usually effective for probe hybridization. A blocking agent is then added. Mixing is continued at room temperature for 1 hour, then the mixture is heated to 42° C. for 0.5–1 hour with occasional mixing.

If necessary, the hybridization buffer may be pre-heated to 42° C. The DNA-containing blots are then placed in the buffer and allowed to prehybridize for at least 15 minutes at 42° C. with gentle agitation. A 1 hour prehybridization is routinely used. Hybridization is carried out in an appropriate container with sufficient hybridization buffer.

Following pre-hybridization, a labeled probe, such as a DNA probe corresponding to nucleotides 1061 to 1163 of FIG. 5, is added to the pre-hybridization buffer. Incubation of the blot with the probe is continued with gentle agitation overnight at 42° C.

The primary wash buffer (with or without urea) is then prepared as set forth below and is preheated to 42° C. The primary wash buffer is used in excess at a volume of approximately 2–5 ml/cm$^2$ of membrane. The blot is transferred to the primary wash buffer and is washed for 20 minutes with gentle agitation, ensuring that the temperature does not exceed 42° C. If necessary, a further wash in fresh primary wash buffer at 42° C. for 20 minutes is carried out.

Stringency may be altered by the SSC concentration in both types of primary wash buffers set forth below. In the present example, 0.5×SSC is considered to be low stringency, and 0.1×SSC is considered to be high stringency.

Next, the blot is placed in a clean container and an excess of secondary wash buffer (prepared as set forth below) is added. The blot is then washed with gentle agitation for 5 minutes at room temperature. Another wash is carried out in fresh secondary wash buffer at room temperature for 5 minutes.

The presence of the RIB1 gene is then detected by known methods in the art, e.g., by exposing X-ray film with the blot containing bound radio-labeled probe or detected fluorometrically e.g., by detecting a fluorescently labeled probe.

Primary wash buffer containing urea 6M urea 0.4% Sodiumdodecylsulphate 0.5×SSC

Primary wash buffer without urea
  0.4% Sodiumdodecylsulphate
  0.5×SSC
Secondary wash buffer
  2×SSC
SSC
  15 mM Sodium citrate
  150 mM NaCl
  pH7.0

The invention being thus described, it will be obvious that the same may be viewed in many ways. Such variations are not to be regarded as a departure from the spirit and scope of the invention and all such modifications are intended to be included within the scope of the following claims.

SEQUENCE LISTING

```
<160> NUMBER OF SEQ ID NOS: 12

<210> SEQ ID NO 1
<211> LENGTH: 2181
<212> TYPE: DNA
<213> ORGANISM: Candida guilliermondii
<220> FEATURE:
<221> NAME/KEY: misc_feature
<222> LOCATION: (1450)..(1659)
<223> OTHER INFORMATION: autonomously replicating sequence
<220> FEATURE:
<221> NAME/KEY: CDS
<222> LOCATION: (474)..(1472)
<223> OTHER INFORMATION: translated portion of the RIB1 gene

<400> SEQUENCE: 1
gtcgactttc actccgaagg taggtgcggc tggaagacgt cgtcccaagt cgtatgcgtt      60
agctgagagc gacggaaacg aaagtgatga agattacatg ctggaataat ccatagctag     120
tgtacttgct aatacaaccg gtaaagctag ccaattgcag cgttattcac caccgccgtg     180
gatcgggtta gtcacgtgaa ctggccgttg ggtcctgcac gtcgcttcat tattcatata     240
ttagtgagag tcttcctata tcagtcagca gacgtatcgg ttgatttcag gtcaaaaaga     300
gaaaaggtgg tcttacaaaa gcgaaatagc tgatacattt ttactcacag cagcatcata     360
tttgtggaac ctttaaactt gacttttcat ttcaagcaag ttattttgaa attcaaatca     420
tttggaaatc aaaaaagaac atctaagttc tgaaaaattg tacgaacaac gct atg         476
                                                            Met
                                                             1 gca tcg aag gac ata gta cat ccg caa cca gag cgc cgg cac ggg tcg        524
Ala Ser Lys Asp Ile Val His Pro Gln Pro Glu Arg Arg His Gly Ser
        5                  10                  15 gaa act cac gaa ttt acc atg cct ctc tta tct cct aca ttg aca cca        572
Glu Thr His Glu Phe Thr Met Pro Leu Leu Ser Pro Thr Leu Thr Pro
     20                  25                  30 tcc cat att cca tcg caa acg cct caa att cct ccg gaa gtg cca gca        620
Ser His Ile Pro Ser Gln Thr Pro Gln Ile Pro Pro Glu Val Pro Ala
 35                  40                  45 gaa gtc agg gat cgc ttg ccc ctt cct gaa acg ttg cct gtg gtg aaa        668
Glu Val Arg Asp Arg Leu Pro Leu Pro Glu Thr Leu Pro Val Val Lys
 50                  55                  60                  65 tgc atg gcg aga gct cgt ata ccg acc act cag ggg ccg gag ata ttt        716
Cys Met Ala Arg Ala Arg Ile Pro Thr Thr Gln Gly Pro Glu Ile Phe
                 70                  75                  80 ctc cat ttg tac gag aat aac gtt gac aat aaa gag cat ttg gct att        764
Leu His Leu Tyr Glu Asn Asn Val Asp Asn Lys Glu His Leu Ala Ile
             85                  90                  95 gtt ttt ggg gaa gat gtg cgg tcg aaa acg ctc tat cag aaa cgt ccc        812
Val Phe Gly Glu Asp Val Arg Ser Lys Thr Leu Tyr Gln Lys Arg Pro
         100                 105                 110 aat gag acc cag caa gat aga atg act cgt ggt gct tat gtg ggc aga        860
Asn Glu Thr Gln Gln Asp Arg Met Thr Arg Gly Ala Tyr Val Gly Arg
```

```
           115                 120                 125
ttg ttt cct gga aga acc gag gca gac tat gac agt gag tct aat ttg    908
Leu Phe Pro Gly Arg Thr Glu Ala Asp Tyr Asp Ser Glu Ser Asn Leu
130                 135                 140                 145 aga ttg aat ttc gat gaa aat ggc caa ctt atc aga gat ccg agt acc    956
Arg Leu Asn Phe Asp Glu Asn Gly Gln Leu Ile Arg Asp Pro Ser Thr
                150                 155                 160 acc tgt agt ggt gag ccc att ttg gcc cgt att cat tcg gaa tgt tat   1004
Thr Cys Ser Gly Glu Pro Ile Leu Ala Arg Ile His Ser Glu Cys Tyr
                165                 170                 175 acg ggg gaa acc gca tgg agt gct cgt tgc gat tgt gga gaa caa ttc   1052
Thr Gly Glu Thr Ala Trp Ser Ala Arg Cys Asp Cys Gly Glu Gln Phe
                180                 185                 190 gat gaa gct ggt cgg tta atg ggt gaa gct ggg cac ggg tgt atc gtg   1100
Asp Glu Ala Gly Arg Leu Met Gly Glu Ala Gly His Gly Cys Ile Val
195                 200                 205 tac ctt cgt cag gaa ggt cgt gga att gga ctt ggg gaa aag ttg aag   1148
Tyr Leu Arg Gln Glu Gly Arg Gly Ile Gly Leu Gly Glu Lys Leu Lys
210                 215                 220                 225 gct tat aat ttg caa gac ttg gga gcg gat acc gtc cag gcc aat ttg   1196
Ala Tyr Asn Leu Gln Asp Leu Gly Ala Asp Thr Val Gln Ala Asn Leu
                230                 235                 240 atg tta cga cat cct gct gat gcg aga tct ttt tcg ctc gct aca gcc   1244
Met Leu Arg His Pro Ala Asp Ala Arg Ser Phe Ser Leu Ala Thr Ala
                245                 250                 255 ata ctc ttg gac ttg ggg ctc aac gag atc aag ttg ttg acc aac aat   1292
Ile Leu Leu Asp Leu Gly Leu Asn Glu Ile Lys Leu Leu Thr Asn Asn
                260                 265                 270 ccc gat aaa att gct gca gtt gag gga aga aac aga gag gtc aag gta   1340
Pro Asp Lys Ile Ala Ala Val Glu Gly Arg Asn Arg Glu Val Lys Val
275                 280                 285 gtg gaa cgg gtg cct atg gtg ccg ttg gca tgg aga agt gag aat gga   1388
Val Glu Arg Val Pro Met Val Pro Leu Ala Trp Arg Ser Glu Asn Gly
290                 295                 300                 305 atc aag tca aaa gag ata gag ggc tac ttg agt gct aag att gaa agg   1436
Ile Lys Ser Lys Glu Ile Glu Gly Tyr Leu Ser Ala Lys Ile Glu Arg
                310                 315                 320 atg ggg cac ttg ctt gaa aag cca ctc aag ata tga tagaagagat        1482
Met Gly His Leu Leu Glu Lys Pro Leu Lys Ile
                325                 330 gaagttaagg acttaagaaa taaatgatga attaaatgac gcaaatgtca ctactcgatt  1542
agagaaatag ctataatgaa gaattttgca tttcgcaaaa tttaagataa atgcaaaaat  1602
tgcaaattac gaaatatgca tatgatacaa gacaagaaaa gactactaaa agtctctcga  1662
gaagaatact gggtaacctt catctcttga ttatgcactg gggctattca tatgcagatt  1722
cgcacgccga ggtgcagcgt ttaggcgcgg ctcaacggaa gccaacgcc gcccacaaatt  1782 gtccggaaag tcgccgaaac tgatccactg gtaccacagc cccataagaa ccccctttaa  1842
tattaaaaac cgttcttcag ccactttga tcacattgtt tgcagccgcc cgttgctgcc   1902
atccaaacac cacgcgtccc ccgcaccttt tacggtgccc actgcattgg aatttgcata  1962
aaacagcctc acgaagtgga ttaatttta gagcactcaa gtcatcatgc tgcaatctct   2022
gcatcatgaa atgactcccg ttgatacagg gaactcagac cgcaagcggc gaagagtcac  2082
aagagcgtgt gatgtgtgtc gactctagag atccccgggt accgagctcg aattcactgg  2142
ccgtcgtttt acaacgtcgt gactgggaaa accctggcg                        2181
```

```
<210> SEQ ID NO 2
<211> LENGTH: 332
<212> TYPE: PRT
<213> ORGANISM: Candida guilliermondii

<400> SEQUENCE: 2

Met Ala Ser Lys Asp Ile Val His Pro Gln Pro Glu Arg Arg His Gly
 1               5                  10                  15

Ser Glu Thr His Glu Phe Thr Met Pro Leu Leu Ser Pro Thr Leu Thr
                20                  25                  30

Pro Ser His Ile Pro Ser Gln Thr Pro Gln Ile Pro Pro Glu Val Pro
            35                  40                  45

Ala Glu Val Arg Asp Arg Leu Pro Leu Pro Glu Thr Leu Pro Val Val
        50                  55                  60

Lys Cys Met Ala Arg Ala Arg Ile Pro Thr Thr Gln Gly Pro Glu Ile
 65                  70                  75                  80

Phe Leu His Leu Tyr Glu Asn Asn Val Asp Asn Lys Glu His Leu Ala
                85                  90                  95

Ile Val Phe Gly Glu Asp Val Arg Ser Lys Thr Leu Tyr Gln Lys Arg
            100                 105                 110

Pro Asn Glu Thr Gln Gln Asp Arg Met Thr Arg Gly Ala Tyr Val Gly
        115                 120                 125

Arg Leu Phe Pro Gly Arg Thr Glu Ala Asp Tyr Asp Ser Glu Ser Asn
130                 135                 140

Leu Arg Leu Asn Phe Asp Glu Asn Gly Gln Leu Ile Arg Asp Pro Ser
145                 150                 155                 160

Thr Thr Cys Ser Gly Glu Pro Ile Leu Ala Arg Ile His Ser Glu Cys
                165                 170                 175

Tyr Thr Gly Glu Thr Ala Trp Ser Ala Arg Cys Asp Cys Gly Glu Gln
            180                 185                 190

Phe Asp Glu Ala Gly Arg Leu Met Gly Glu Ala Gly His Gly Cys Ile
        195                 200                 205

Val Tyr Leu Arg Gln Glu Gly Arg Gly Ile Gly Leu Gly Glu Lys Leu
    210                 215                 220

Lys Ala Tyr Asn Leu Gln Asp Leu Gly Ala Asp Thr Val Gln Ala Asn
225                 230                 235                 240

Leu Met Leu Arg His Pro Ala Asp Ala Arg Ser Phe Ser Leu Ala Thr
                245                 250                 255

Ala Ile Leu Leu Asp Leu Gly Leu Asn Glu Ile Lys Leu Leu Thr Asn
            260                 265                 270

Asn Pro Asp Lys Ile Ala Ala Val Glu Gly Arg Asn Arg Glu Val Lys
        275                 280                 285

Val Val Glu Arg Val Pro Met Val Pro Leu Ala Trp Arg Ser Glu Asn
    290                 295                 300

Gly Ile Lys Ser Lys Glu Ile Glu Gly Tyr Leu Ser Ala Lys Ile Glu
305                 310                 315                 320

Arg Met Gly His Leu Leu Glu Lys Pro Leu Lys Ile
                325                 330

<210> SEQ ID NO 3
<211> LENGTH: 2264
<212> TYPE: DNA
<213> ORGANISM: Artificial Sequence
<220> FEATURE:
<223> OTHER INFORMATION: Description of Artificial Sequence:
      Amplified DNA containing parts of the complete TEF promoter of
      S. cerevisiae and the 5' part of the C.
``` guilliermondii RIB1 gene
<220> FEATURE:
<221> NAME/KEY: promoter
<222> LOCATION: (1)..(552)
<223> OTHER INFORMATION: TEF promoter fragment
<220> FEATURE:
<221> NAME/KEY: CDS
<222> LOCATION: (557)..(1555)
<223> OTHER INFORMATION: translated portion of RIB1 gene

<400> SEQUENCE: 3

```
caattcgagc tcgtacccg  gggatccccc acacaccata gcttcaaaat gtttctactc      60 ctttttact  cttccagatt ttctcggact ccgcgcatcg ccgtaccact tcaaaacacc     120
caagcacagc atactaaatt ccctctcttc ttcctctagg gtgtcgttaa ttacccgtac     180
taaaggtttg gaaagaaaa  aagagaccgc ctcgtttctt tttcttcgtc gaaaaaggca     240
ataaaaattt ttatcacgtt tctttttctt gaaatttttt tttttgattt ttttctcttt     300
cgatgacctc ccattgatat ttaagtcaat aaacggtctt caatttctca gtttcagtt     360 tcatttttct tgttctatta caactttttt tacttcttgc tcattagaaa gaaagcatag     420
caatctaatc taagggcgag ctcgaattcg aactagtact gcagcacgtg accggcgcct     480
agtgttgaca attaatcatc ggcatagtat atcggcatag tataatacga ctcactatag     540
gaggaagctt ggcgct atg gca tcg aag tac ata gta cat ccg caa cca gag      592
                    Met Ala Ser Lys Tyr Ile Val His Pro Gln Pro Glu
                     1               5                  10 cgc cgg cac ggg tcg gaa act cac gaa ttt acc atg cct ctc tta tct       640
Arg Arg His Gly Ser Glu Thr His Glu Phe Thr Met Pro Leu Leu Ser
         15                  20                  25 cct aca ttg aca cca tcc cat att cca tcg caa acg cct caa att cct       688
Pro Thr Leu Thr Pro Ser His Ile Pro Ser Gln Thr Pro Gln Ile Pro
 30                  35                  40 ccg gaa gtg cca gca gaa gtc agg gat cgc ttg ccc ctt cct gaa acg       736
Pro Glu Val Pro Ala Glu Val Arg Asp Arg Leu Pro Leu Pro Glu Thr
 45                  50                  55                  60 ttg cct gtg gtg aaa tgc atg gcg aga gct cgt ata ccg acc act cag       784
Leu Pro Val Val Lys Cys Met Ala Arg Ala Arg Ile Pro Thr Thr Gln
                 65                  70                  75 ggg ccg gag ata ttt ctc cat ttg tac gag aat aac gtt gac aat aaa       832
Gly Pro Glu Ile Phe Leu His Leu Tyr Glu Asn Asn Val Asp Asn Lys
         80                  85                  90 gag cat ttg gct att gtt ttt ggg gaa gat gtg cgg tcg aaa acg ctc       880
Glu His Leu Ala Ile Val Phe Gly Glu Asp Val Arg Ser Lys Thr Leu
                 95                 100                 105 tat cag aaa cgt ccc aat gag acc cag caa gat aga atg act cgt ggt       928
Tyr Gln Lys Arg Pro Asn Glu Thr Gln Gln Asp Arg Met Thr Arg Gly
    110                 115                 120 gct tat gtg ggc aga ttg ttt cct gga aga acc gag gca gac tat gac       976
Ala Tyr Val Gly Arg Leu Phe Pro Gly Arg Thr Glu Ala Asp Tyr Asp
125                 130                 135                 140 agt gag tct aat ttg aga ttg aat ttc gat gaa aat ggc caa ctt atc      1024
Ser Glu Ser Asn Leu Arg Leu Asn Phe Asp Glu Asn Gly Gln Leu Ile
                145                 150                 155 aga gat ccg agt acc acc tgt agt ggt gag ccc att ttg gcc cgt att      1072
Arg Asp Pro Ser Thr Thr Cys Ser Gly Glu Pro Ile Leu Ala Arg Ile
    160                 165                 170 cat tcg gaa tgt tat acg ggg gaa acc gca tgg agt gct cgt tgc gat      1120
His Ser Glu Cys Tyr Thr Gly Glu Thr Ala Trp Ser Ala Arg Cys Asp
        175                 180                 185 tgt gga gaa caa ttc gat gaa gct ggt cgg tta atg ggt gaa gct ggg      1168
```

```
Cys Gly Glu Gln Phe Asp Glu Ala Gly Arg Leu Met Gly Glu Ala Gly
        190                 195                 200 cac ggg tgt atc gtg tac ctt cgt cag gaa ggt cgt gga att gga ctt      1216
His Gly Cys Ile Val Tyr Leu Arg Gln Glu Gly Arg Gly Ile Gly Leu
205                 210                 215                 220 ggg gaa aag ttg aag gct tat aat ttg caa gac ttg gga gcg gat acc      1264
Gly Glu Lys Leu Lys Ala Tyr Asn Leu Gln Asp Leu Gly Ala Asp Thr
                225                 230                 235 gtc cag gcc aat ttg atg tta cga cat cct gct gat gcg aga tct ttt      1312
Val Gln Ala Asn Leu Met Leu Arg His Pro Ala Asp Ala Arg Ser Phe
    240                 245                 250 tcg ctc gct aca gcc ata ctc ttg gac ttg ggg ctc aac gag atc aag      1360
Ser Leu Ala Thr Ala Ile Leu Leu Asp Leu Gly Leu Asn Glu Ile Lys
                255                 260                 265 ttg ttg acc aac aat ccc gat aaa att gct gca gtt gag gga aga aac      1408
Leu Leu Thr Asn Asn Pro Asp Lys Ile Ala Ala Val Glu Gly Arg Asn
270                 275                 280 aga gag gtc aag gta gtg gaa cgg gtg cct atg gtg ccg ttg gca tgg      1456
Arg Glu Val Lys Val Val Glu Arg Val Pro Met Val Pro Leu Ala Trp
285                 290                 295                 300 aga agt gag aat gga atc aag tca aaa gag ata gag ggc tac ttg agt      1504
Arg Ser Glu Asn Gly Ile Lys Ser Lys Glu Ile Glu Gly Tyr Leu Ser
                305                 310                 315 gct aag att gaa agg atg ggg cac ttg ctt gaa aag cca ctc aag ata      1552
Ala Lys Ile Glu Arg Met Gly His Leu Leu Glu Lys Pro Leu Lys Ile
        320                 325                 330 tga tagaagagat gaagttaagg acttaagaaa taaatgatga attaaatgac           1605
gcaaatgtca ctactcgatt agagaaatag ctataatgaa gaattttgca tttcgcaaaa    1665
tttaagataa atgcaaaaat tgcaaattac gaaatatgca tatgatacaa gacaagaaaa    1725
gactactaaa agtctctcga gaagaatact gggtaacctt catctcttga ttatgcactg    1785
gggctattca tatgcagatt cgcacgccga ggtgcagcgt ttaggcgcgg ctcaacggaa    1845
gccaacggcc gccacaaatt gtccggaaag tcgccgaaac tgatccactg gtaccacagc    1905
cccataagaa ccccctttaa tattaaaaac cgttcttcag ccacttttga tcacattgtt    1965
tgcagccgcc cgttgctgcc atccaaacac cacgcgtccc ccgcaccttt tacggtgccc    2025
actgcattgg aatttgcata aaacagcctc acgaagtgga ttaattttta gagcactcaa    2085
gtcatcatgc tgcaatctct gcatcatgaa atgactcccg ttgatacagg gaactcagac    2145
cgcaagcggg gaagagtcac aagagcgtgt gatgtgtgtc gactctagag atccccgggt    2205
accgagctcg aattcactgg ccgtcgtttt acaacgtcgt gactgggaaa accctggcg     2264

<210> SEQ ID NO 4
<211> LENGTH: 332
<212> TYPE: PRT
<213> ORGANISM: Artificial Sequence

<400> SEQUENCE: 4

Met Ala Ser Lys Tyr Ile Val His Pro Gln Pro Glu Arg Arg His Gly
1               5                   10                  15

Ser Glu Thr His Glu Phe Thr Met Pro Leu Leu Ser Pro Thr Leu Thr
            20                  25                  30

Pro Ser His Ile Pro Ser Gln Thr Pro Gln Ile Pro Pro Glu Val Pro
        35                  40                  45

Ala Glu Val Arg Asp Arg Leu Pro Leu Pro Glu Thr Leu Pro Val Val
    50                  55                  60
```

Lys Cys Met Ala Arg Ala Arg Ile Pro Thr Thr Gln Gly Pro Glu Ile
 65                  70                  75                  80

Phe Leu His Leu Tyr Glu Asn Asn Val Asp Asn Lys Glu His Leu Ala
                 85                  90                  95

Ile Val Phe Gly Glu Asp Val Arg Ser Lys Thr Leu Tyr Gln Lys Arg
            100                 105                 110

Pro Asn Glu Thr Gln Gln Asp Arg Met Thr Arg Gly Ala Tyr Val Gly
        115                 120                 125

Arg Leu Phe Pro Gly Arg Thr Glu Ala Asp Tyr Asp Ser Glu Ser Asn
    130                 135                 140

Leu Arg Leu Asn Phe Asp Glu Asn Gly Gln Leu Ile Arg Asp Pro Ser
145                 150                 155                 160

Thr Thr Cys Ser Gly Glu Pro Ile Leu Ala Arg Ile His Ser Glu Cys
                165                 170                 175

Tyr Thr Gly Glu Thr Ala Trp Ser Ala Arg Cys Asp Cys Gly Glu Gln
            180                 185                 190

Phe Asp Glu Ala Gly Arg Leu Met Gly Glu Ala Gly His Gly Cys Ile
        195                 200                 205

Val Tyr Leu Arg Gln Glu Gly Arg Gly Ile Gly Leu Gly Glu Lys Leu
    210                 215                 220

Lys Ala Tyr Asn Leu Gln Asp Leu Gly Ala Asp Thr Val Gln Ala Asn
225                 230                 235                 240

Leu Met Leu Arg His Pro Ala Asp Ala Arg Ser Phe Ser Leu Ala Thr
                245                 250                 255

Ala Ile Leu Leu Asp Leu Gly Leu Asn Glu Ile Lys Leu Leu Thr Asn
            260                 265                 270

Asn Pro Asp Lys Ile Ala Ala Val Glu Gly Arg Asn Arg Glu Val Lys
        275                 280                 285

Val Val Glu Arg Val Pro Met Val Pro Leu Ala Trp Arg Ser Glu Asn
    290                 295                 300

Gly Ile Lys Ser Lys Glu Ile Glu Gly Tyr Leu Ser Ala Lys Ile Glu
305                 310                 315                 320

Arg Met Gly His Leu Leu Glu Lys Pro Leu Lys Ile
                325                 330

<210> SEQ ID NO 5
<211> LENGTH: 1742
<212> TYPE: DNA
<213> ORGANISM: Artificial Sequence
<220> FEATURE:
<223> OTHER INFORMATION: Description of Artificial Sequence:
      Nucleotide sequence of the pTCdXS-2 insert
<220> FEATURE:
<221> NAME/KEY: promoter
<222> LOCATION: (1)..(552)
<223> OTHER INFORMATION: TEF promoter fragment
<220> FEATURE:
<221> NAME/KEY: misc_feature
<222> LOCATION: (1533)..(1742)
<223> OTHER INFORMATION: autonomously replicating sequence
<220> FEATURE:
<221> NAME/KEY: CDS
<222> LOCATION: (557)..(1555)
<223> OTHER INFORMATION: translated portion of RIB1 gene

<400> SEQUENCE: 5
caattcgagc tcggtacccg gggatccccc acacaccata gcttcaaaat gtttctactc    60
cttttttact cttccagatt ttctcggact ccgcgcatcg ccgtaccact tcaaaacacc   120
caagcacagc atactaaatt tccctctttc ttcctctagg gtgtcgttaa ttacccgtac   180

```
taaaggtttg gaaagaaaaa aagagaccgc ctcgtttctt tttcttcgtc gaaaaaggca    240
ataaaaattt ttatcacgtt tcttttctt gaaattttt tttttgattt ttttctcttt      300
cgatgacctc ccattgatat ttaagtcaat aaacggtctt caatttctca agtttcagtt    360
tcatttttct tgttctatta caactttttt tacttcttgc tcattagaaa gaaagcatag    420
caatctaatc taagggcgag ctcgaattcg aactagtact gcagcacgtg accggcgcct    480
agtgttgaca attaatcatc ggcatagtat atcggcatag tataatacga ctcactatag    540
gaggaagctt ggcgct atg gca tcg aag tac ata gta cat ccg caa cca gag    592
              Met Ala Ser Lys Tyr Ile Val His Pro Gln Pro Glu
                1               5                  10 cgc cgg cac ggg tcg gaa act cac gaa ttt acc atg cct ctc tta tct      640
Arg Arg His Gly Ser Glu Thr His Glu Phe Thr Met Pro Leu Leu Ser
        15                  20                  25 cct aca ttg aca cca tcc cat att cca tcg caa acg cct caa att cct      688
Pro Thr Leu Thr Pro Ser His Ile Pro Ser Gln Thr Pro Gln Ile Pro
    30                  35                  40 ccg gaa gtg cca gca gaa gtc agg gat cgc ttg ccc ctt cct gaa acg      736
Pro Glu Val Pro Ala Glu Val Arg Asp Arg Leu Pro Leu Pro Glu Thr
45                  50                  55                  60 ttg cct gtg gtg aaa tgc atg gcg aga gct cgt ata ccg acc act cag      784
Leu Pro Val Val Lys Cys Met Ala Arg Ala Arg Ile Pro Thr Thr Gln
                65                  70                  75 ggg ccg gag ata ttt ctc cat ttg tac gag aat aac gtt gac aat aaa      832
Gly Pro Glu Ile Phe Leu His Leu Tyr Glu Asn Asn Val Asp Asn Lys
            80                  85                  90 gag cat ttg gct att gtt ttt ggg gaa gat gtg cgg tcg aaa acg ctc      880
Glu His Leu Ala Ile Val Phe Gly Glu Asp Val Arg Ser Lys Thr Leu
        95                  100                 105 tat cag aaa cgt ccc aat gag acc cag caa gat aga atg act cgt ggt      928
Tyr Gln Lys Arg Pro Asn Glu Thr Gln Gln Asp Arg Met Thr Arg Gly
    110                 115                 120 gct tat gtg ggc aga ttg ttt cct gga aga acc gag gca gac tat gac      976
Ala Tyr Val Gly Arg Leu Phe Pro Gly Arg Thr Glu Ala Asp Tyr Asp
125                 130                 135                 140 agt gag tct aat ttg aga ttg aat ttc gat gaa aat ggc caa ctt atc     1024
Ser Glu Ser Asn Leu Arg Leu Asn Phe Asp Glu Asn Gly Gln Leu Ile
                145                 150                 155 aga gat ccg agt acc acc tgt agt ggt gag ccc att ttg gcc cgt att     1072
Arg Asp Pro Ser Thr Thr Cys Ser Gly Glu Pro Ile Leu Ala Arg Ile
            160                 165                 170 cat tcg gaa tgt tat acg ggg gaa acc gca tgg agt gct cgt tgc gat     1120
His Ser Glu Cys Tyr Thr Gly Glu Thr Ala Trp Ser Ala Arg Cys Asp
        175                 180                 185 tgt gga gaa caa ttc gat gaa gct ggt cgg tta atg ggt gaa gct ggg     1168
Cys Gly Glu Gln Phe Asp Glu Ala Gly Arg Leu Met Gly Glu Ala Gly
    190                 195                 200 cac ggg tgt atc gtg tac ctt cgt cag gaa ggt cgt gga att gga ctt     1216
His Gly Cys Ile Val Tyr Leu Arg Gln Glu Gly Arg Gly Ile Gly Leu
205                 210                 215                 220 ggg gaa aag ttg aag gct tat aat ttg caa gac ttg gga gcg gat acc     1264
Gly Glu Lys Leu Lys Ala Tyr Asn Leu Gln Asp Leu Gly Ala Asp Thr
                225                 230                 235 gtc cag gcc aat ttg atg tta cga cat cct gct gat gcg aga tct ttt     1312
Val Gln Ala Asn Leu Met Leu Arg His Pro Ala Asp Ala Arg Ser Phe
            240                 245                 250 tcg ctc gct aca gcc ata ctc ttg gac ttg ggg ctc aac gag atc aag     1360
Ser Leu Ala Thr Ala Ile Leu Leu Asp Leu Gly Leu Asn Glu Ile Lys
```

-continued

```
              255                 260                 265
ttg ttg acc aac aat ccc gat aaa att gct gca gtt gag gga aga aac      1408
Leu Leu Thr Asn Asn Pro Asp Lys Ile Ala Ala Val Glu Gly Arg Asn
        270                 275                 280 aga gag gtc aag gta gtg gaa cgg gtg cct atg gtg ccg ttg gca tgg      1456
Arg Glu Val Lys Val Val Glu Arg Val Pro Met Val Pro Leu Ala Trp
285                 290                 295                 300 aga agt aag aat gga atc aag tca aaa gag ata gag ggc tac ttg agt      1504
Arg Ser Lys Asn Gly Ile Lys Ser Lys Glu Ile Glu Gly Tyr Leu Ser
                305                 310                 315 gct aag att gaa agg atg ggg cac ttg ctt gaa aag cca ctc aag ata      1552
Ala Lys Ile Glu Arg Met Gly His Leu Leu Glu Lys Pro Leu Lys Ile
            320                 325                 330 tga tagaagagat gaagttaagg acttaagaaa taatgatga attaaatgac            1605 gcaaatgtca ctactcgatt agagaaatag ctataatgaa gaattttgca tttcgcaaaa    1665
tttaagataa atgcaaaaat tgcaaattac gaaatatgca tatgatacaa gacaagaaaa    1725
gactactaaa agtctct                                                    1742

<210> SEQ ID NO 6
<211> LENGTH: 332
<212> TYPE: PRT
<213> ORGANISM: Artificial Sequence

<400> SEQUENCE: 6

Met Ala Ser Lys Tyr Ile Val His Pro Gln Pro Glu Arg Arg His Gly
 1               5                  10                  15

Ser Glu Thr His Glu Phe Thr Met Pro Leu Leu Ser Pro Thr Leu Thr
            20                  25                  30

Pro Ser His Ile Pro Ser Gln Thr Pro Gln Ile Pro Pro Glu Val Pro
        35                  40                  45

Ala Glu Val Arg Asp Arg Leu Pro Leu Pro Glu Thr Leu Pro Val Val
    50                  55                  60

Lys Cys Met Ala Arg Ala Arg Ile Pro Thr Thr Gln Gly Pro Glu Ile
65                  70                  75                  80

Phe Leu His Leu Tyr Glu Asn Asn Val Asp Asn Lys Glu His Leu Ala
                85                  90                  95

Ile Val Phe Gly Glu Asp Val Arg Ser Lys Thr Leu Tyr Gln Lys Arg
            100                 105                 110

Pro Asn Glu Thr Gln Gln Asp Arg Met Thr Arg Gly Ala Tyr Val Gly
        115                 120                 125

Arg Leu Phe Pro Gly Arg Thr Glu Ala Asp Tyr Asp Ser Glu Ser Asn
    130                 135                 140

Leu Arg Leu Asn Phe Asp Glu Asn Gly Gln Leu Ile Arg Asp Pro Ser
145                 150                 155                 160

Thr Thr Cys Ser Gly Glu Pro Ile Leu Ala Arg Ile His Ser Glu Cys
                165                 170                 175

Tyr Thr Gly Glu Thr Ala Trp Ser Ala Arg Cys Asp Cys Gly Glu Gln
            180                 185                 190

Phe Asp Glu Ala Gly Arg Leu Met Gly Glu Ala Gly His Gly Cys Ile
        195                 200                 205

Val Tyr Leu Arg Gln Glu Gly Arg Gly Ile Gly Leu Gly Glu Lys Leu
    210                 215                 220

Lys Ala Tyr Asn Leu Gln Asp Leu Gly Ala Asp Thr Val Gln Ala Asn
225                 230                 235                 240
```

```
Leu Met Leu Arg His Pro Ala Asp Ala Arg Ser Phe Ser Leu Ala Thr
            245                 250                 255

Ala Ile Leu Leu Asp Leu Gly Leu Asn Glu Ile Lys Leu Leu Thr Asn
            260                 265                 270

Asn Pro Asp Lys Ile Ala Ala Val Glu Gly Arg Asn Arg Glu Val Lys
            275                 280                 285

Val Val Glu Arg Val Pro Met Val Pro Leu Ala Trp Arg Ser Lys Asn
    290                 295                 300

Gly Ile Lys Ser Lys Glu Ile Glu Gly Tyr Leu Ser Ala Lys Ile Glu
305                 310                 315                 320

Arg Met Gly His Leu Leu Glu Lys Pro Leu Lys Ile
            325                 330

<210> SEQ ID NO 7
<211> LENGTH: 1175
<212> TYPE: DNA
<213> ORGANISM: Artificial Sequence
<220> FEATURE:
<223> OTHER INFORMATION: Description of Artificial Sequence:
      PCR fragment containing base pairs 1-1,168 of the  pTCdXS-2
      insert.
<220> FEATURE:
<221> NAME/KEY: promoter
<222> LOCATION: (8)..(559)
<223> OTHER INFORMATION: TEF promoter fragment
<220> FEATURE:
<221> NAME/KEY: CDS
<222> LOCATION: (564)..(1172)
<223> OTHER INFORMATION: partially translated portion of RIB1 gene

<400> SEQUENCE: 7
gggcatgcaa ttcgagctcg gtacccgggg atcccccaca caccatagct tcaaaatgtt     60
tctactcctt ttttactctt ccagattttc tcggactccg cgcatcgccg taccacttca    120
aaacacccaa gcacagcata ctaaatttcc ctctttcttc ctctagggtg tcgttaatta    180
cccgtactaa aggtttggaa agaaaaaag agaccgcctc gtttcttttt cttcgtcgaa     240
aaaggcaata aaaattttta tcacgtttct ttttcttgaa attttttttt ttgatttttt    300
tctctttcga tgacctccca ttgatattta agtcaataaa cggtcttcaa tttctcaagt    360
ttcagtttca tttttcttgt tctattacaa cttttttttac ttcttgctca ttagaaagaa   420
agcatagcaa tctaatctaa gggcgagctc gaattcgaac tagtactgca gcacgtgacc    480
ggcgcctagt gttgacaatt aatcatcggc atagtatatc ggcatagtat aatacgactc    540
actataggag gaagcttggc gct atg gca tcg aag tac ata gta cat ccg caa    593
                            Met Ala Ser Lys Tyr Ile Val His Pro Gln
                             1               5                  10 cca gag cgc cgg cac ggg tcg gaa act cac gaa ttt acc atg cct ctc     641
Pro Glu Arg Arg His Gly Ser Glu Thr His Glu Phe Thr Met Pro Leu
            15                  20                  25 tta tct cct aca ttg aca cca tcc cat att cca tcg caa acg cct caa     689
Leu Ser Pro Thr Leu Thr Pro Ser His Ile Pro Ser Gln Thr Pro Gln
        30                  35                  40 att cct ccg gaa gtg cca gca gaa gtc agg gat cgc ttg ccc ctt cct     737
Ile Pro Pro Glu Val Pro Ala Glu Val Arg Asp Arg Leu Pro Leu Pro
    45                  50                  55 gaa acg ttg cct gtg gtg aaa tgc atg gcg aga gct cgt ata ccg acc     785
Glu Thr Leu Pro Val Val Lys Cys Met Ala Arg Ala Arg Ile Pro Thr
60                  65                  70 act cag ggg ccg gag ata ttt ctc cat ttg tac gag aat aac gtt gac     833
Thr Gln Gly Pro Glu Ile Phe Leu His Leu Tyr Glu Asn Asn Val Asp
        75                  80                  85                  90
```

```
aat aaa gag cat ttg gct att gtt ttt ggg gaa gat gtg cgg tcg aaa      881
Asn Lys Glu His Leu Ala Ile Val Phe Gly Glu Asp Val Arg Ser Lys
            95                  100                 105 acg ctc tat cag aaa cgt ccc aat gag acc cag caa gat aga atg act      929
Thr Leu Tyr Gln Lys Arg Pro Asn Glu Thr Gln Gln Asp Arg Met Thr
        110                 115                 120 cgt ggt gct tat gtg ggc aga ttg ttt cct gga aga acc gag gca gac      977
Arg Gly Ala Tyr Val Gly Arg Leu Phe Pro Gly Arg Thr Glu Ala Asp
            125                 130                 135 tat gac agt gag tct aat ttg aga ttg aat ttc gat gaa aat ggc caa     1025
Tyr Asp Ser Glu Ser Asn Leu Arg Leu Asn Phe Asp Glu Asn Gly Gln
    140                 145                 150 ctt atc aga gat ccg agt acc acc tgt agt ggt gag ccc att ttg gcc     1073
Leu Ile Arg Asp Pro Ser Thr Thr Cys Ser Gly Glu Pro Ile Leu Ala
155                 160                 165                 170 cgt att cat tcg gaa tgt tat acg ggg gaa acc gca tgg agt gct cgt     1121
Arg Ile His Ser Glu Cys Tyr Thr Gly Glu Thr Ala Trp Ser Ala Arg
                175                 180                 185 tgc gat tgt gga gaa caa ttc gat gaa gct ggt cgg tta atg ggt gaa     1169
Cys Asp Cys Gly Glu Gln Phe Asp Glu Ala Gly Arg Leu Met Gly Glu
            190                 195                 200 gct ggg                                                              1175
Ala

<210> SEQ ID NO 8
<211> LENGTH: 203
<212> TYPE: PRT
<213> ORGANISM: Artificial Sequence

<400> SEQUENCE: 8

Met Ala Ser Lys Tyr Ile Val His Pro Gln Pro Glu Arg Arg His Gly
 1               5                  10                  15

Ser Glu Thr His Glu Phe Thr Met Pro Leu Leu Ser Pro Thr Leu Thr
            20                  25                  30

Pro Ser His Ile Pro Ser Gln Thr Pro Gln Ile Pro Pro Glu Val Pro
        35                  40                  45

Ala Glu Val Arg Asp Arg Leu Pro Leu Pro Glu Thr Leu Pro Val Val
    50                  55                  60

Lys Cys Met Ala Arg Ala Arg Ile Pro Thr Thr Gln Gly Pro Glu Ile
65                  70                  75                  80

Phe Leu His Leu Tyr Glu Asn Asn Val Asp Asn Lys Glu His Leu Ala
                85                  90                  95

Ile Val Phe Gly Glu Asp Val Arg Ser Lys Thr Leu Tyr Gln Lys Arg
            100                 105                 110

Pro Asn Glu Thr Gln Gln Asp Arg Met Thr Arg Gly Ala Tyr Val Gly
        115                 120                 125

Arg Leu Phe Pro Gly Arg Thr Glu Ala Asp Tyr Asp Ser Glu Ser Asn
    130                 135                 140

Leu Arg Leu Asn Phe Asp Glu Asn Gly Gln Leu Ile Arg Asp Pro Ser
145                 150                 155                 160

Thr Thr Cys Ser Gly Glu Pro Ile Leu Ala Arg Ile His Ser Glu Cys
                165                 170                 175

Tyr Thr Gly Glu Thr Ala Trp Ser Ala Arg Cys Asp Cys Gly Glu Gln
            180                 185                 190

Phe Asp Glu Ala Gly Arg Leu Met Gly Glu Ala
        195                 200
```

```
<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence:
      PGgtpCY_nco Primer

<400> SEQUENCE: 9
gctggtcggt taatgggtga agctggg                                        27

<210> SEQ ID NO 10
<211> LENGTH: 31
<212> TYPE: DNA
<213> ORGANISM: Artificial Sequence
<220> FEATURE:
<223> OTHER INFORMATION: Description of Artificial Sequence:  PGgtpCY_V
      Primer

<400> SEQUENCE: 10
aggaggaagc ttggcgctat ggcatcgaag g                                   31

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence:  ShBle_V
      Primer

<400> SEQUENCE: 11
gggcatgcaa ttcgagctcg gtacccg                                        27

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence:
      TEF1_H Primer

<400> SEQUENCE: 12
cgactcacta taggaggaag cttggcgc                                       28
```

What is claimed is:

1. A purified and isolated DNA molecule comprising a polynucleotide sequence encoding SEQ ID NO:6.

2. The purified and isolated DNA molecule of claim 1 wherein the polynucleotide sequence comprises SEQ ID NO:5.

3. The purified and isolated DNA molecule of claim 2 wherein the polynucleotide sequence consists of SEQ ID NO:5.

4. The purified and isolated DNA molecule of claim 1 wherein the DNA molecule is transcriptionally linked to a promoter.

5. The purified and isolated DNA molecule of claim 4 wherein the promoter is the TEF promoter from S. cerevisiae.

6. The purified and isolated DNA molecule of claim 2 wherein the DNA molecule is transcriptionally linked to a promoter.

7. The purified and isolated DNA molecule of claim 6 wherein the promoter is the TEF promoter from S. cerevisiae.

8. A yeast strain transformed with a polynucleotide sequence encoding SEQ ID NO:6.

9. The yeast strain according to claim 8 wherein the polynucleotide sequence is SEQ ID NO:5.

10. The yeast strain according to claim 8 further comprising a promoter transcriptionally linked to the polynucleotide sequence, wherein the promoter is not naturally linked to the polynucleotide sequence but is functional in the yeast strain.

11. The yeast strain according to claim 10 wherein the promoter is the TEF promoter from S. cerevisiae.

12. The yeast strain according to claim 9 further comprising a promoter transcriptionally linked to SEQ ID NO:5, wherein the promoter is not naturally linked to SEQ ID NO:5 but is functional in the yeast strain.

13. The yeast strain according to claim 12 wherein the promoter is the TEF S. cerevisiae promoter.

14. The yeast strain according to claim 8 wherein the transformed yeast strain is a flavinogenic yeast which overproduces riboflavin under conditions of iron starvation.

15. The yeast strain of claim 14 wherein the transformed yeast strain is selected from the group consisting of Schwanniomyces, Debaryomyces, Torulopsis, and Candida.

16. The yeast strain of claim 15 wherein the transformed yeast strain is selected from the group consistently of

*Schwanniomyces occidentalis, Debaryomyces kloeckeri, Torulopsis candida, Candida guilliermondii* and *Candida famata*.

17. The yeast strain of claim 15 wherein the transformed yeast strain is selected from the group of *Candida guilliermondii* and *Candida famata*.

18. A process for producing a polypeptide comprising the sequence of SEQ ID NO:6, which process comprises:
   (a) incorporating into an expression cassette a polynucleotide sequence encoding SEQ ID NO:6;
   (b) transforming a yeast cell culture selected front the group consisting of Schwanniomyces, Debaryomyces, Torulopsis, and Candida with the expression cassette;
   (c) selecting a transformant which produces SEQ ID) NO:6;
   (d) culturing the transformant selected in step (c) in a culture medium; and
   (e) recovering the polypeptide from the transformant and/or the culture medium.

19. The process according to claim 18 wherein the polypeptide recovered in step (e) consists of SEQ ID NO:6.

20. The process according to claim 18 wherein the polynucleotide sequence comprises SEQ ID NO:5.

21. The process according to claim 18 wherein the expression cassette comprises a promoter transcriptionally linked to the polynucleotide sequence, wherein the promoter is not naturally linked to the polynucleofide sequence but is functional in the yeast cell.

22. The process according to claim 21 wherein the promoter is the TEF promoter from *S. cerevisiae*.

23. The process according to claim 20 wherein the expression cassette comprises a promoter transcriptionally linked to SEQ ID NO:5, wherein the promoter is not naturally linked to SEQ ID NO:5 but is functional in the yeast cell.

24. The process according to claim 23 wherein the promoter is the TEF promoter from *S. cerevisiae*.

25. A process for producing riboflavin comprising:
   (a) incorporating into an expression cassette a DNA sequence which encodes SEQ ID NO:6;
   (b) transforming a yeast cell culture selected from the group consisting of Schwanniomyces, Debaryomyces, Torulopsis, and Candida with the expression cassette;
   (c) selecting a transformant which overproduces riboflavin;
   (d) culturing the transformant in a culture medium; and
   (e) recovering riboflavin from the transformant and/or the culture medium.

26. The process according to claim 25 wherein the DNA sequence comprises SEQ ID NO:5.

27. The process according to claim 25 wherein the expression cassette comprises a promoter transcriptionally linked to the DNA sequence, wherein the promoter is not naturally linked to the DNA sequence but is functional in the yeast cell.

28. The process according to claim 27 wherein the promoter is the TEF promoter from *S. cerevisiae*.

29. The process according to claim 26 wherein the expression cassette comprises a promoter transcriptionally linked to SEQ ID NO:5, wherein the promoter is not naturally linked to SEQ ID NO:5 but is functional in the yeast cell.

30. The process according to claim 29 wherein the promoter is the TEF promoter from *S. cerevisiae*.

31. The process according to claim 25 further comprising mixing the recovered riboflavin with a food or feed ingredient to produce a food or feed composition.

* * * * *

UNITED STATES PATENT AND TRADEMARK OFFICE
CERTIFICATE OF CORRECTION

PATENT NO.    : 6,376,222 B1
DATED         : April 23, 2002
INVENTOR(S)   : Lyubov Ya. Babyak et al.

It is certified that error appears in the above-identified patent and that said Letters Patent is hereby corrected as shown below:

<u>Title page,</u>
Item [73], Assignee, please change "Parsipanny" to -- Parsippany --;
"*Primary Examiner*," please change "Ponnathapuachuta Murthy" to
-- Ponnathapu Achutamurthy --;

<u>Column 34,</u>
Line 65, please italicize "Schwanniomyces", "Debaryomyces", "Torulopsis",
and "Candida";
Line 67, please change "consistently" to -- consisting --;

<u>Column 35,</u>
Line 11, please change "front" to -- from --;
Lines 12 and 13, please italicize "Schwanniomyces", "Debaryomyces", "Torulopsis",
and "Candida";
Line 14, please delete the ")" after "ID";
Line 27, please change "polynucleofide" to -- polynucleotide --;

<u>Column 36,</u>
Lines 8 and 9, please italicize "Schwanniomyces", "Debaryomyces", "Torulopsis",
and "Candida".

Signed and Sealed this

Seventh Day of January, 2003

JAMES E. ROGAN
*Director of the United States Patent and Trademark Office*